(12) United States Patent
Matsuda et al.

(10) Patent No.: US 11,950,970 B2
(45) Date of Patent: Apr. 9, 2024

(54) MEDICAL SUPPORT ARM SYSTEM, MEDICAL SUPPORT ARM CONTROL METHOD, AND MEDICAL SUPPORT ARM CONTROL DEVICE

(71) Applicant: SONY GROUP CORPORATION, Tokyo (JP)

(72) Inventors: Yasuhiro Matsuda, Tokyo (JP); Fumiyasu Suzuki, Saitama (JP); Atsushi Miyamoto, Kanagawa (JP); Yohei Kuroda, Tokyo (JP); Kenichiro Nagasaka, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/655,060

(22) Filed: Mar. 16, 2022

(65) Prior Publication Data

US 2022/0211464 A1     Jul. 7, 2022

Related U.S. Application Data

(63) Continuation of application No. 16/615,908, filed as application No. PCT/JP2018/015393 on Apr. 12, 2018.

(30) Foreign Application Priority Data

May 31, 2017   (JP) .................. 2017-107681

(51) Int. Cl.
*A61B 90/50* (2016.01)
*A61B 34/30* (2016.01)
(Continued)

(52) U.S. Cl.
CPC ............ *A61B 90/50* (2016.02); *B25J 9/12* (2013.01); *B25J 9/1633* (2013.01); *B25J 9/1689* (2013.01);
(Continued)

(58) Field of Classification Search
CPC ... A61B 90/50; A61B 34/25; A61B 2090/371; A61B 2090/508; A61B 2090/066;
(Continued)

(56) References Cited

U.S. PATENT DOCUMENTS

| 5,767,648 A | 6/1998 | Morel et al. |
| 6,723,106 B1 | 4/2004 | Charles et al. |

(Continued)

FOREIGN PATENT DOCUMENTS

| JP | 07-261843 A | 10/1995 |
| JP | 2009-047503 A | 3/2009 |

(Continued)

OTHER PUBLICATIONS

Corke, Peter I. et al., "Robotics, vision and control: fundamental algorithms in MATLAB", 2011, Springer, vol. 73. Berlin, pp. 191-218. (Year: 2011).*

(Continued)

*Primary Examiner* — Jaime Figueroa
(74) *Attorney, Agent, or Firm* — CHIP LAW GROUP

(57) ABSTRACT

Provided is a medical support arm system including a support arm that is a multilink structure having a plurality of links connected by a joint unit including an actuator, and supports a medical unit. The medical support arm system further includes a control device including an external force estimation unit to estimate an external force acting on the joint unit on the basis of a drive characteristic of the actuator, and a joint control unit to control drive of the joint unit on the basis of an external torque estimated by the external force estimation unit.

7 Claims, 12 Drawing Sheets

(51) Int. Cl.
  *B25J 9/12* (2006.01)
  *B25J 9/16* (2006.01)
  *A61B 34/00* (2016.01)
  *A61B 90/00* (2016.01)
(52) U.S. Cl.
  CPC ......... *A61B 34/25* (2016.02); *A61B 2090/371* (2016.02)
(58) Field of Classification Search
  CPC  A61B 2017/00402; A61B 2017/00398; A61B 2034/2059; A61B 90/25; A61B 34/30; B25J 9/12; B25J 9/1633; B25J 9/1689; B25J 13/085; G05B 2219/40184; G05B 2219/40194
  USPC ................................................ 700/245–264
  See application file for complete search history.

(56) References Cited

U.S. PATENT DOCUMENTS

| | | | | |
|---|---|---|---|---|
| 6,999,851 | B2* | 2/2006 | Kato | G06N 3/008 318/568.14 |
| 7,872,436 | B2* | 1/2011 | Kock | G05B 13/025 318/568.22 |
| 8,340,822 | B2* | 12/2012 | Nagasaka | B25J 9/1633 700/170 |
| 8,442,685 | B2* | 5/2013 | Ooga | B25J 9/1633 318/568.22 |
| 8,874,262 | B2 | 10/2014 | Mistry | |
| 9,242,375 | B2* | 1/2016 | Orita | B25J 9/0015 |
| 9,539,059 | B2 | 1/2017 | Fukushima et al. | |
| 10,029,369 | B1* | 7/2018 | Carlisle | B25J 9/042 |
| 10,252,420 | B2* | 4/2019 | Carlisle | B25J 13/085 |
| 10,335,959 | B2 | 7/2019 | Ogata | |
| 10,405,931 | B2 | 9/2019 | Fukushima et al. | |
| 10,493,617 | B1 | 12/2019 | Holson et al. | |
| 11,007,025 | B2 | 5/2021 | Randle | |
| 2004/0133308 | A1* | 7/2004 | Kato | G06N 3/008 700/258 |
| 2006/0071625 | A1* | 4/2006 | Nakata | B25J 9/1633 318/568.12 |
| 2006/0207419 | A1* | 9/2006 | Okazaki | F15B 11/20 91/35 |
| 2007/0260356 | A1* | 11/2007 | Kock | G05B 13/025 901/30 |
| 2009/0024142 | A1 | 1/2009 | Ruiz Morales | |
| 2009/0272585 | A1* | 11/2009 | Nagasaka | B25J 9/1633 74/490.03 |
| 2011/0060460 | A1* | 3/2011 | Oga | B25J 9/1633 700/254 |
| 2012/0022690 | A1* | 1/2012 | Ooga | B25J 9/1633 700/258 |
| 2012/0150347 | A1* | 6/2012 | Ohga | B25J 9/1633 700/254 |
| 2012/0239198 | A1* | 9/2012 | Orita | B25J 9/1633 700/260 |
| 2013/0073084 | A1* | 3/2013 | Ooga | B25J 9/02 700/254 |
| 2013/0079930 | A1 | 3/2013 | Mistry | |
| 2013/0245829 | A1* | 9/2013 | Ohta | B25J 9/1641 901/9 |
| 2014/0195052 | A1 | 7/2014 | Tsusaka et al. | |
| 2014/0228862 | A1 | 8/2014 | Inoue et al. | |
| 2014/0276952 | A1 | 9/2014 | Hourtash et al. | |
| 2015/0250547 | A1 | 9/2015 | Fukushima et al. | |
| 2015/0313679 | A1 | 11/2015 | Fukushima et al. | |
| 2016/0156297 | A1 | 6/2016 | Takase et al. | |
| 2016/0263749 | A1 | 9/2016 | Ogata | |
| 2017/0007336 | A1 | 1/2017 | Tsuboi et al. | |
| 2017/0079729 | A1 | 3/2017 | Fukushima et al. | |
| 2017/0112580 | A1 | 4/2017 | Griffiths et al. | |
| 2017/0367774 | A1 | 12/2017 | Scholan | |
| 2018/0008359 | A1 | 1/2018 | Randle | |
| 2018/0021094 | A1 | 1/2018 | Matsuda et al. | |
| 2018/0079090 | A1 | 3/2018 | Koenig et al. | |
| 2018/0232593 | A1* | 8/2018 | Tani | F16P 3/142 |
| 2018/0289445 | A1* | 10/2018 | Krinninger | A61B 90/37 |
| 2018/0354135 | A1* | 12/2018 | Carlisle | B25J 9/1676 |
| 2019/0015175 | A1* | 1/2019 | Tamura | B25J 9/1697 |
| 2019/0216555 | A1 | 7/2019 | Dimaio et al. | |
| 2019/0350661 | A1 | 11/2019 | Fukushima et al. | |
| 2019/0365489 | A1* | 12/2019 | Kasai | G01L 5/00 |
| 2019/0388179 | A1* | 12/2019 | Krinninger | A61B 90/50 |
| 2020/0001459 | A1 | 1/2020 | Song | |
| 2020/0281671 | A1 | 9/2020 | Randle | |
| 2021/0347039 | A1 | 11/2021 | Paine et al. | |

FOREIGN PATENT DOCUMENTS

| | | |
|---|---|---|
| JP | 2010-076012 A | 4/2010 |
| JP | 2012-024877 A | 2/2012 |
| WO | 2015/046081 A1 | 4/2015 |
| WO | WO-2015046081 A1 * | 4/2015 ............... A61B 1/04 |

OTHER PUBLICATIONS

International Search Report and Written Opinion of PCT Application No. PCT/JP2018/015393, dated Jun. 12, 2018, 09 pages of English Translation and 09 pages of ISRWO.

International Preliminary Report on Patentability of PCT Application No. PCT/JP2018/015393, dated Dec. 12, 2019, 09 pages of English Translation and 05 pages of IPRP.

Notice of Allowance for U.S. Appl. No. 16/615,908, dated Dec. 17, 2021, 13 pages.

Non-Final Office Action for U.S. Appl. No. 16/615,908, dated Aug. 5, 2021, 17 pages.

* cited by examiner

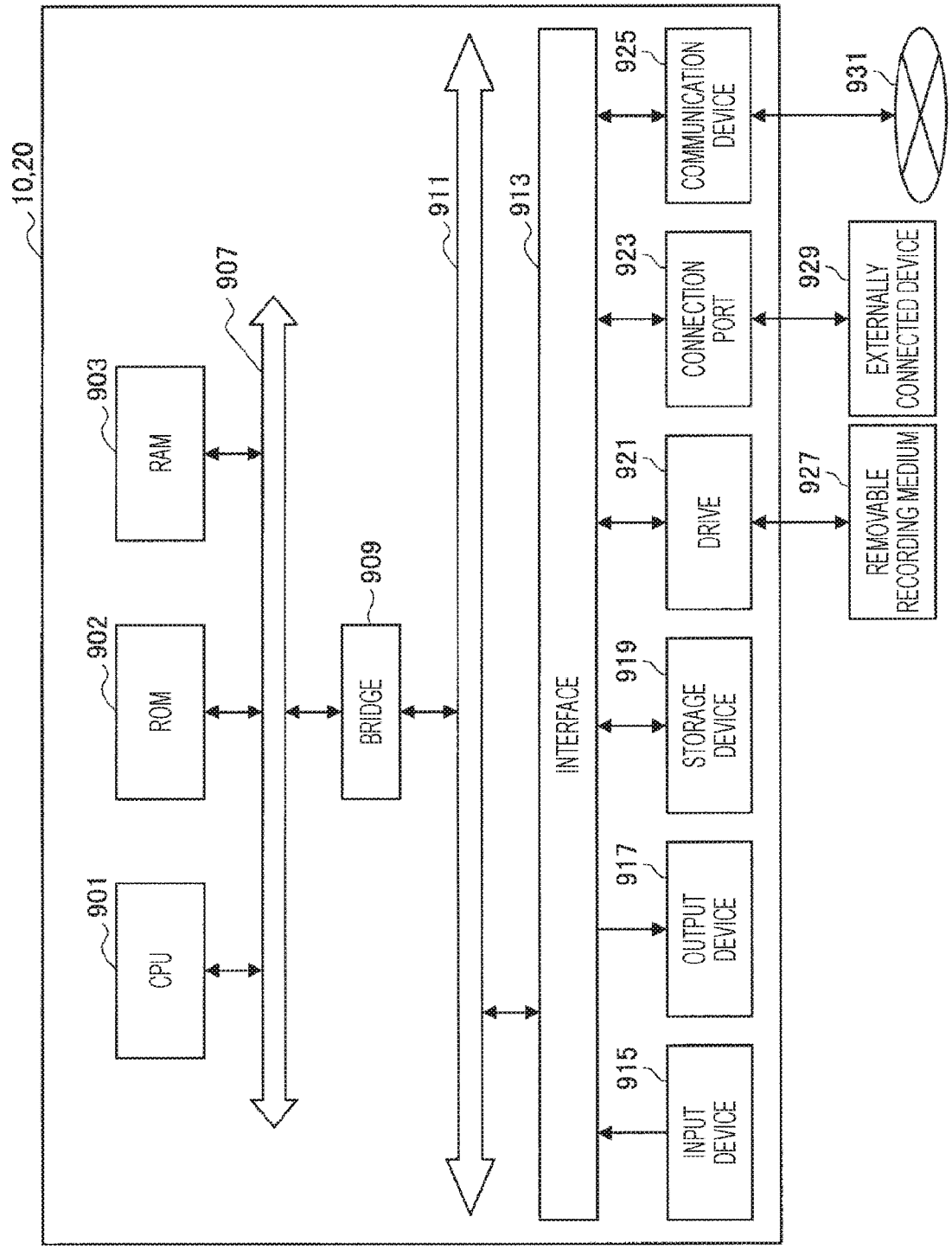

MEDICAL SUPPORT ARM SYSTEM, MEDICAL SUPPORT ARM CONTROL METHOD, AND MEDICAL SUPPORT ARM CONTROL DEVICE

The present application is a continuation application of U.S. patent application Ser. No. 16/615,908 filed Nov. 22, 2019, which is a national stage entry of PCT/JP2018/015393, filed Apr. 12, 2018, which claims priority from prior Japanese Priority Patent Application JP 2017-107681 filed in the Japan Patent Office on May 31, 2017 the entire contents of which are hereby incorporated by reference.

TECHNICAL FIELD

The present disclosure relates to a medical support arm system, a medical support arm control method, and a medical support arm control device.

BACKGROUND ART

Conventionally, in the medical field, there are cases where a medical device having a medical unit (a camera, forceps, or the like) provided at a distal end of an arm unit is used when various operations (surgery, inspection, and the like) are performed. For example, Patent Document 1 below discloses a torque-controlled medical arm that is controlled on the basis of force information detected by a torque sensor incorporated in an actuator unit.

Meanwhile, methods of performing force control without using a torque sensor as described above have also been proposed. For example, Patent Document 2 below discloses a tactile analysis method based on an estimated reaction force. Furthermore, Patent Document 3 below discloses a control device that performs force control on the basis of an estimated gripping force.

CITATION LIST

Patent Document

Patent Document 1: International Publication No. 2015/046081
Patent Document 2: Japanese Patent Application Laid-Open No. 2009-47503
Patent Document 3: Japanese Patent Application Laid-Open No. 2010-76012

SUMMARY OF THE INVENTION

Problems to be Solved by the Invention

Here, in ideal response control related to the medical arm as described in Patent Document 1, improvement of the total cost of the device can be assumed by using an estimated torque value according to the situation. However, the techniques disclosed in Patent Documents 2 and 3 above are not related to torque estimation, and are difficult to apply to the ideal response control of the medical arm as described in Patent Document 1.

Therefore, the present disclosure proposes new and improved medical support arm system, medical support arm control method, and medical support arm control device that realize torque control based on an estimated external force and can cope with more various situations.

Solutions to Problems

According to the present disclosure, provided is a medical support arm system including: a support arm that is a multilink structure having a plurality of links connected by a joint unit including an actuator, and configured to support a medical unit; and a control device including an external force estimation unit configured to estimate an external force acting on the joint unit on the basis of a drive characteristic of the actuator, and a joint control unit configured to control drive of the joint unit on the basis of an external torque estimated by the external force estimation unit.

Furthermore, according to the present disclosure, provided is a medical support arm control method including: by a processor, controlling drive of a joint unit including an actuator of a support arm that is a multilink structure having a plurality of links connected by the joint unit; and estimating an external force acting on the joint unit on the basis of a drive characteristic of the actuator, in which the controlling further includes controlling the drive of the joint unit on the basis of an estimated external torque.

Furthermore, according to the present disclosure, provided is a medical support arm control device including: a joint control unit configured to control drive of a joint unit including an actuator of a support arm that is a multilink structure having a plurality of links connected by the joint unit; and an external force estimation unit configured to estimate an external force acting on the joint unit on the basis of a drive characteristic of the actuator, in which the joint control unit controls the drive of the joint unit on the basis of an external torque estimated by the external force estimation unit.

Effects of the Invention

As described above, according to the present disclosure, torque control based on an estimated external force is realized and more various situations can be coped with.

Note that the above-described effect is not necessarily limited, and any of effects described in the present specification or other effects that can be grasped from the present specification may be exerted in addition to or in place of the above-described effect.

BRIEF DESCRIPTION OF DRAWINGS

FIG. 14 is a functional block diagram illustrating a configuration example of a hardware configuration of a support arm device and a control device according to an embodiment of the present disclosure.

MODE FOR CARRYING OUT THE INVENTION

Favorable embodiments of the present disclosure will be described in detail with reference to the appended drawings. Note that, in the present specification and drawings, overlapping description of configuration elements having substantially the same functional configuration is omitted by providing the same sign.

Note that the description will be given in the following order.
1. Study of Medical Support Arm Device
2. Embodiment of Present Disclosure
2-1. Appearance of Support Arm Device
2-2. Generalized Inverse Dynamics
2-3. Ideal Joint Control
2-4. Configuration of Support Arm System
3. Hardware Configuration
4. Conclusion 1. Study of Medical Support Arm Device First, to make the present disclosure clearer, the background that the present inventors have conceived the present disclosure will be described.

Figure 1:
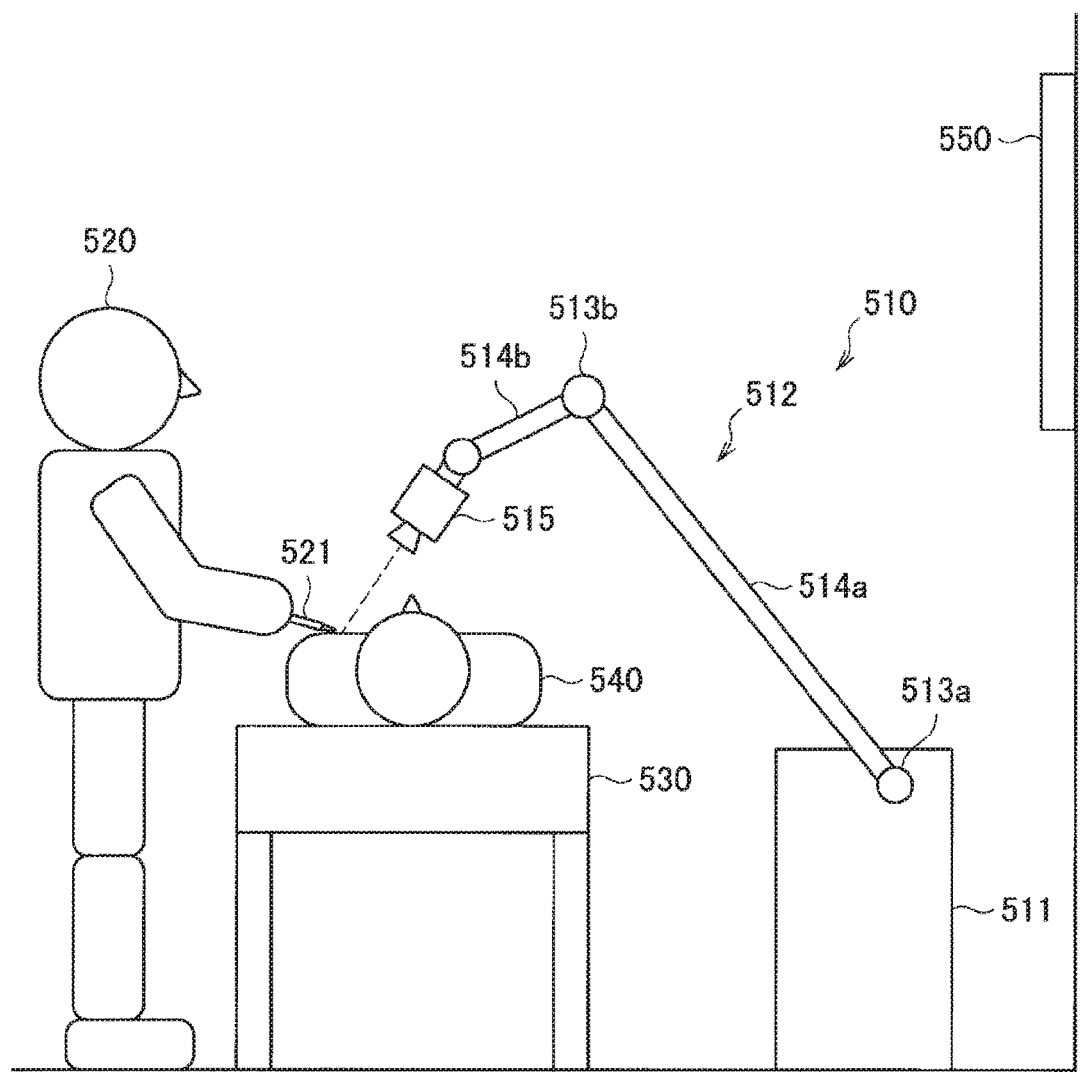
FIG. 1 is an explanatory diagram for describing an application example of a case where a support arm device according to an embodiment of the present disclosure is used for medical purposes.

An application example of a case where a medical support arm device (hereinafter simply referred to as a support arm device or a support arm) according to an embodiment of the present disclosure is used for medical purposes will be described with reference to FIG. 1. FIG. 1 is an explanatory diagram for describing an application example of a case where a support arm device according to an embodiment of the present disclosure is used for medical purposes.

FIG. 1 schematically illustrates a state of an operation using the support arm device according to the present embodiment. Specifically, referring to FIG. 1, a state in which a surgeon who is a practitioner (user) 520 is performing surgery for an operation target (patient) 540 on an operation table 530 using a surgical instrument 521 such as a scalpel, tweezers, or forceps, for example, is illustrated. Note that, in the following description, the term "operation" is a generic term for various types of medical treatment such as surgery and examination performed for the patient as the operation target 540 by a surgeon as the user 520. Furthermore, the example in FIG. 1 illustrates a state of surgery as an example of the operation, but the operation using a support arm device 510 is not limited to surgery, and may be various operations such as an examination using an endoscope.

The support arm device 510 according to the present embodiment is provided beside the operation table 530. The support arm device 510 includes a base unit 511 as a base and an arm unit 512 extending from the base unit 511. The arm unit 512 includes a plurality of joint units 513a, 513b, and 513c, a plurality of links 514a and 514b connected by the joint units 513a and 513b, and an imaging unit 515 provided at a distal end of the arm unit 512. In the example illustrated in FIG. 1, the arm unit 512 includes the three joint units 513a to 513c and the two links 514a and 514b for the sake of simplicity. However, in reality, the numbers and shapes of the joint units 513a to 513c and the links 514a and 514b, the direction of drive shafts of the joint units 513a to 513c, and the like may be appropriately set to realize a desired degree of freedom in consideration of the degrees of freedom in the positions and postures of the arm unit 512 and the imaging unit 515.

The joint units 513a to 513c have a function to rotatably connect the links 514a and 514b to each other, and the drive of the arm unit 512 is controlled when the rotation of the joint units 513a to 513c is driven. Here, in the following description, the position of each configuration member of the support arm device 510 means the position (coordinates) in the space defined for drive control, and the posture of each configuration member means the direction (angle) with respect to any axis in the space defined for drive control. Furthermore, in the following description, drive (or drive control) of the arm unit 512 refers to the position and posture of each configuration member of the arm unit 512 being changed (change being controlled) by drive (drive control) of the joint units 513a to 513c and drive (drive control) of the joint units 513a to 513c.

Various medical instruments are connected to the distal end of the arm unit 512 as distal end units. In the example illustrated in FIG. 1, the imaging unit 515 is provided at the distal end of the arm unit 512 as an example of the distal end unit. The imaging unit 515 is a unit that acquires an image (captured image) of a capture target, and is, for example, a camera or the like that can capture a moving image or a still image. As illustrated in FIG. 1, the positions and postures of the arm unit 512 and the imaging unit 515 are controlled by the support arm device 510 so that the imaging unit 515 provided at the distal end of the arm unit 512 captures a state of the operation site of the operation target 540. Note that the distal end unit provided at the distal end of the arm unit 512 is not limited to the imaging unit 515, and various medical instruments may be provided. Examples of the medical instruments include various units used in operations, such as an endoscope and microscope, units having an imaging function such as the above-described imaging unit 515, and various operation tools and examination devices. Thus, the support arm device 510 according to the present embodiment can be said to be a medical support arm device provided with medical instruments. Furthermore, a stereo camera having two imaging units (camera units) may be provided at the distal end of the arm unit 512 and may capture an imaging target as a three-dimensional image (3D image). Note that the support arm device 510 provided with a camera unit such as the imaging unit 515 or the stereo camera for capturing the operation site as the distal end unit is also referred to as video microscope (VM) support arm device.

Furthermore, at a position facing the user 520, a display device 550 such as a monitor or a display is installed. An image of the operation site captured by the imaging unit 515 is displayed on a display screen of the display device 550. The user 520 performs various types of treatment while viewing the captured image of the operation site displayed on the display screen of the display device 550.

Thus, the present embodiment proposes, in the medical field, performing surgery while capturing an operation site by the support arm device 510. Here, in various operations including surgery, reduction of fatigue and burden on the user 520 and the patient 540 is required by more efficiently performing the operation. To satisfy such requirement, the support arm device 510 is considered to require following performance, for example.

First, as a first point, the support arm device 510 is required to secure a working space in the operation. If the arm unit 512 or the imaging unit 515 obstructs the view of the practitioner or the movement of the hand performing treatment while the user 520 is performing various types of treatment for the operation target 540, the efficiency of the surgery declines. Furthermore, although not illustrated in FIG. 1, in an actual surgery scene, there is generally a plurality of other surgeons, nurses, and the like around the user 520 and the patient 540, who perform various support works such as passing an instrument to the user 520 and checking various vital signs of the patient 540, and also there are other devices to perform the support works. Therefore, the surgical environment is complicated. Therefore, the support arm device 510 is desirably as small as possible.

Next, as a second point, the support arm device 510 is required to have high operability when moving the imaging unit 515. For example, there is the user 520's need to observe the same operation site from various positions and angles while performing the treatment for the operation site, depending on a site for which the user 520 performs surgery or the content of the surgery. To change an angle to observe the operation site, an angle of the imaging unit 515 with respect to the operation site needs to be changed. At that time, it is desirable to change only the angle to capture the operation site while fixing a capture direction of the imaging unit 515 to the operation site (in other words, while capturing the same operation site). Therefore, for example, operability with a higher degree of freedom is required for the support arm device 510, such as a turning motion (pivot motion) using an axis of a cone as a pivot axis, in which the imaging unit 515 moves in a conical surface having the operation site as a vertex in a state where the capture direction of the imaging unit 515 is fixed to the operation site. Note that, since the capture direction of the imaging unit 515 is fixed to the predetermined operation site, the pivot motion is also called point lock motion.

Furthermore, to change the position and angle of the imaging unit 515, a method of moving the imaging unit 515 to a desired position and angle by the user 520 manually moving the arm unit 512 is conceivable, for example. Therefore, operability that enables the movement of the imaging unit 515, the above-described pivot motion, and the like to be easily performed by one hand is desirable.

Furthermore, at the time of surgery, there is also the user 520's need to move a capture center of an image to be captured by the imaging unit 515 from a site where the user 520 is giving treatment to another site (a site where the user 520 will next give treatment, for example) while performing treatment with both hands. Therefore, when changing the position and posture of the imaging unit 515, not only the method of manually controlling drive of the arm unit 512 as described above but also various methods of driving the arm unit 512, such as a method of controlling the drive of the arm unit 512 by an operation input from an input unit such as a pedal, are required.

Thus, as the second performance, the support arm device 510 is required to have high operability that meets the intuition and demands of the user 520, which realizes the above-described pivot motion and easy manual movement.

Finally, as a third point, the support arm device 510 is required to have stability in the drive control of the arm unit 512. The stability of the arm unit 512 with respect to the drive control may be stability of the position and posture of the distal end unit when the arm unit 512 is driven. Furthermore, the stability of the arm unit 512 with respect to the drive control includes smooth movement of the distal end unit and suppression of vibration (damping) when the arm unit 512 is driven. For example, if the position and posture of the imaging unit 515 are not stable in the case where the distal end unit is the imaging unit 515 as in the example illustrated in FIG. 1, the captured image displayed on a display screen of the display device 550 is not stable and may cause discomfort to the user. In particular, when the support arm device 510 is used for surgery, a method of providing a stereo camera including two imaging units (camera units) as the distal end units, and displaying a three-dimensional image (3D image) generated on the basis of a captured image by the stereo camera on the display device 550 can be assumed. In the case where a 3D image is displayed in this way, there is a possibility of inducing a so-called 3D sickness of the user if the position and posture of the stereo camera are unstable. Furthermore, an observation range captured by the imaging unit 515 may be expanded to about ϕ15 mm depending on the site where the treatment is given and the content of the surgery. In the case where the imaging unit 515 enlarges a narrow range and captures the range as described above, a slight vibration of the imaging unit 515 appears as a large shake or blur of the captured image. Therefore, the drive control of the arm unit 512 and the imaging unit 515 requires high positioning accuracy with an allowable range of about 1 mm. Thus, in the drive control of the arm unit 512, responsiveness with high accuracy and high positioning accuracy are required.

The present inventors have examined general existing balance-type arm and support arm device based on position control from the viewpoint of the above three performances.

First, with regard to the securement of the working space for surgery of the first point, the general balance-type arm is usually provided with a counterbalance weight (also referred to as counterweight or balancer) for balancing the force when the arm unit is moved inside a base unit or the like. Therefore, downsizing of the balance-type arm is difficult and it cannot be said that the performance is satisfied.

Furthermore, with regard to the high operability of the second point, in the general balance-type arm, only a part of the drive of the arm unit, for example, only the drive of two shafts for moving the imaging unit on a plane (in a two-dimensional manner) is electrically driven, and the movement of the arm unit and the imaging unit requires manual positioning. Therefore, it cannot be said that the high operability is realized. Furthermore, in the support arm device by general position control, the position control used for the control of the drive of the arm unit, that is, for the control of the position and posture of the imaging unit, is difficult to flexibly respond to an external force and is sometimes called "hard control", and is not suitable for realizing the operability that matches the intuition of the user as required.

Furthermore, with regard to the stability in the drive control of the arm unit of the third point, generally, a joint unit of the arm unit has factors difficult to model, such as friction and inertia. In the general balance-type arm and support arm device by position control, these factors appear as disturbances in the drive control of a joint unit, so even in a case where a theoretically appropriate control value (for example, a current value to be applied to a motor of the joint unit) is provided, desired drive (for example, rotation of a desired angle in the motor of the joint unit) may not be realized, and realization of the high stability in the drive control of the arm unit as required is difficult.

As described above, as a result of the study about the support arm device used for medical purposes, the present inventors have found that there is a demand for the above-described three performances regarding the support arm device. However, the general existing balance-type arm and support arm device based on position control are difficult to satisfy these performances. As a result of study about a configuration that satisfies the above-described three performances, the present inventors have conceived a support arm device, a support arm control device, a support arm system, a support arm control method, and a program according to the present disclosure. Hereinafter, favorable embodiments in the configuration conceived by the present inventors will be described in detail.

2. Embodiment of Present Disclosure

Hereinafter, a support arm system according to an embodiment of the present disclosure will be described. The support arm system according to the present embodiment controls drive of a plurality of joint units provided in a support arm device by whole body coordination control using generalized inverse dynamics. Moreover, the support arm system applies ideal joint control for realizing an ideal response to a command value by correcting an influence of disturbance to the drive control of the joint units.

In the following description of the present embodiment, first, an appearance of the support arm device according to the present embodiment will be described in [2-1. Appearance of Support Arm Device] and a schematic configuration of the support arm device will be described. Next, an outline of the generalized inverse dynamics and the ideal joint control used in the control of the support arm device according to the present embodiment will be described in [2-2. Generalized Inverse Dynamics] and [2-3. Ideal Joint Control]. Next, in [2-4. Configuration of Support Arm System], a configuration of a system for controlling the support arm device according to the present embodiment will be described using a functional block diagram.

Note that, in the description below, a case in which a distal end unit of an arm unit of the support arm device is an imaging unit, and an operation site is captured by the imaging unit at the time of surgery as illustrated in FIG. 1 will be described as an embodiment of the present disclosure. However, the present embodiment is not limited to the example. The support arm system according to the present embodiment is applicable even in a case where a support arm device having another distal end unit is used for other purposes.

[2-1. Appearance of Support Arm Device]

Figure 2:
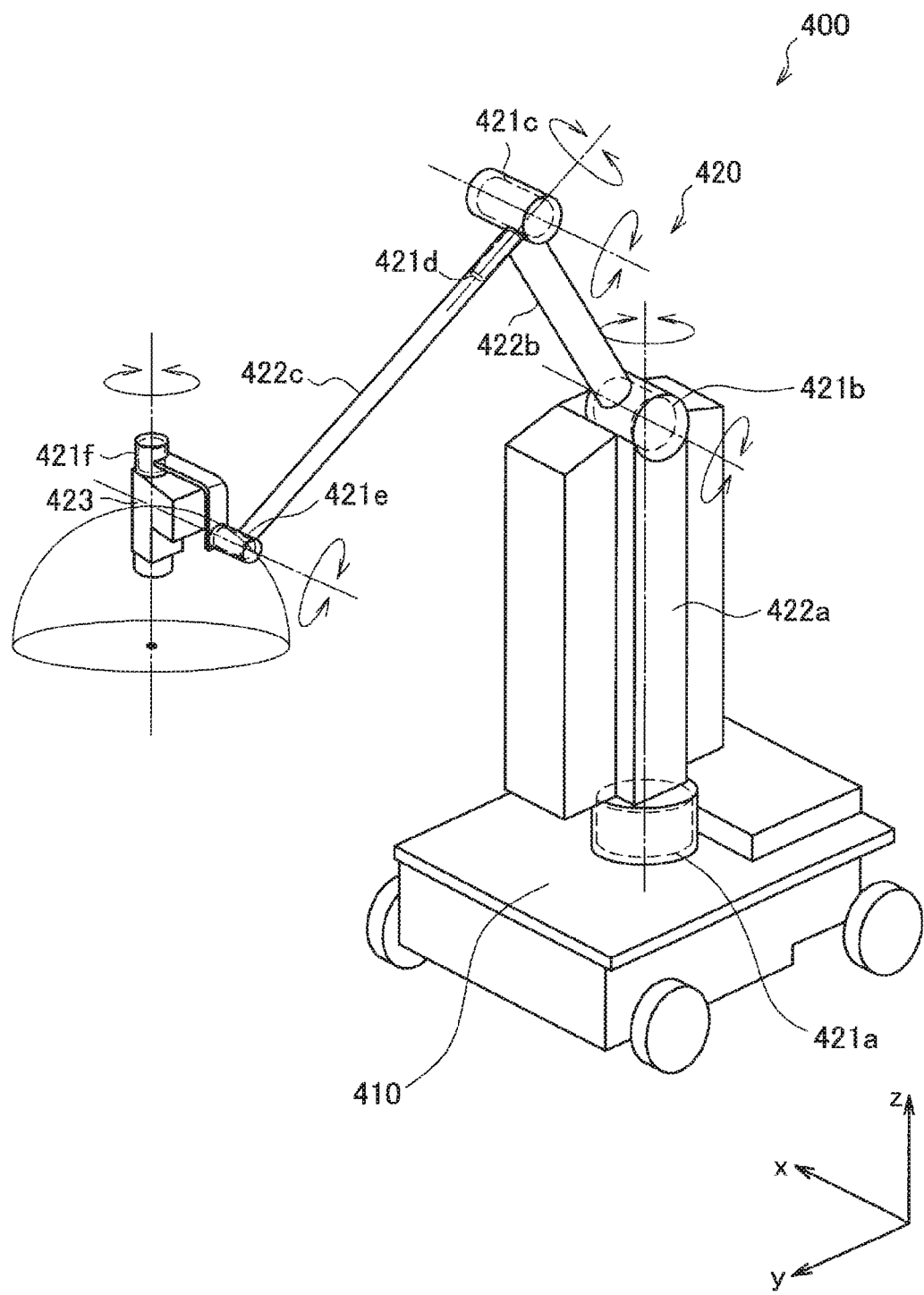
FIG. 2 is a schematic view illustrating an appearance of the support arm device according to an embodiment of the present disclosure.

First, a schematic configuration of a support arm device according to an embodiment of the present disclosure will be described with reference to FIG. 2. FIG. 2 is a schematic view illustrating an appearance of the support arm device according to an embodiment of the present disclosure.

Referring to FIG. 2, a support arm device 400 according to the present embodiment includes a base unit 410 and an arm unit 420. The base unit 410 is a base of the support arm device 400, and the arm unit 420 is extended from the base unit 410. Furthermore, although not illustrated in FIG. 2, a control unit that integrally controls the support arm device 400 may be provided in the base unit 410, and drive of the arm unit 420 may be controlled by the control unit. The control unit is configured by, for example, various signal processing circuits such as a central processing unit (CPU) and a digital signal processor (DSP).

The arm unit 420 includes a plurality of joint units 421a to 421f, a plurality of links 422a to 422c mutually connected by the joint units 421a to 421f, and an imaging unit 423 provided at the distal end of the arm unit 420.

The links 422a to 422c are rod-like members, and one end of the link 422a is connected to the base unit 410 via the joint unit 421a, the other end of the link 422a is connected to one end of the link 422b via the joint unit 421b, and moreover, the other end of the link 422b is connected to one end of the link 422c via the joint units 421c and 421d. Moreover, the imaging unit 423 is connected to the distal end of the arm unit 420, in other words, the other end of the link 422c via the joint units 421e and 421f. As described above, the ends of the plurality of links 422a to 422c are connected one another by the joint units 421a to 421f with the base unit 410 as a fulcrum, so that an arm shape extended from the base unit 410 is configured.

The imaging unit 423 is a unit that acquires an image of a capture target, and is, for example, a camera or the like that captures a moving image or a still image. When drive of the arm unit 420 is controlled, the position and posture of the imaging unit 423 are controlled. In the present embodiment, the imaging unit 423 captures a partial region of a body of a patient, which is an operation site, for example. Note that the distal end unit provided at the distal end of the arm unit 420 is not limited to the imaging unit 423, and various medical instruments may be connected to the distal end of the arm unit 420 as the distal end units. Thus, the support arm device 400 according to the present embodiment can be said to be a medical support arm device provided with medical instruments.

Here, hereinafter, the support arm device 400 will be described by defining coordinate axes as illustrated in FIG. 2. Furthermore, an up-down direction, a front-back direction, and a right-left direction will be defined in accordance with the coordinate axes. In other words, the up-down direction with respect to the base unit 410 installed on a floor is defined as a z-axis direction and the up-down direction. Furthermore, a direction orthogonal to the z axis and in which the arm unit 420 is extended from the base unit 410 (in other words, a direction in which the imaging unit 423 is located with respect to the base unit 410) is defined as a y-axis direction and the front-back direction. Moreover, a direction orthogonal to the y axis and the z axis is defined as an x-axis direction and the right-left direction.

The joint units 421a to 421f rotatably connect the links 422a to 422c to one another. The joint units 421a to 421f include actuators, and have a rotation mechanism that is rotationally driven about a predetermined rotation axis by drive of the actuators. By controlling rotational drive of each of the joint units 421a to 421f, drive of the arm unit 420 such as extending or contracting (folding) of the arm unit 420 can be controlled. Here, the drive of the joint units 421a to 421f is controlled by whole body coordination control to be described in [2-2. Generalized Inverse Dynamics] below and by ideal joint control to be described in [2-3. Ideal Joint Control] below. Furthermore, as described above, since the joint units 421a to 421f have the rotation mechanism, in the following description, the drive control of the joint units 421a to 421f specifically means control of a rotation angle and/or a generated torque of the joint units 421a to 421f (torque generated in the joint units 421a to 421f).

The support arm device 400 according to the present embodiment includes the six joint units 421a to 421f and realizes six degrees of freedom with respect to the drive of the arm unit 420. Specifically, as illustrated in FIG. 2, the joint units 421a, 421d, and 421f are provided to have long axis directions of the connected links 422a to 422c and a capture direction of the connected imaging unit 423 as rotation axis directions, and the joint units 421b, 421c, and 421e are provided to have the x-axis direction that is a direction of changing connection angles of the links 422a to 422c and the imaging unit 423 in a y-z plane (a plane defined by the y axis and the z axis) as the rotation axis directions. As described above, in the present embodiment, the joint units 421a, 421d, and 421f have a function to perform so-called yawing, and the joint units 421b, 421c, and 421e have a function to perform so-called pitching.

With such a configuration of the arm unit 420, the support arm device 400 according to the present embodiment realizes the six degrees of freedom with respect to the drive of the arm unit 420, thereby freely moving the imaging unit 423 within a movable range of the arm unit 420. FIG. 2 illustrates a hemisphere as an example of the movable range of the imaging unit 423. In a case where a central point of the hemisphere is a capture center of the operation site captured by the imaging unit 423, the operation site can be captured from various angles by moving the imaging unit 423 on a spherical surface of the hemisphere in a state where the capture center of the imaging unit 423 is fixed to the central point of the hemisphere.

A schematic configuration of the support arm device 400 according to the present embodiment will be described with reference to FIG. 2. Next, the whole body coordination control and the ideal joint control for controlling the driving of the arm unit 420, in other words, the driving of the joint units 421a to 421f in the support arm device 400 according to the present embodiment will be described.

[2-2. Generalized Inverse Dynamics]

Next, an outline of the generalized inverse dynamics used for the whole body coordination control of the support arm device 400 in the present embodiment will be described.

The generalized inverse dynamics is basic arithmetic operation in the whole body coordination control of a multilink structure configured by connecting a plurality of links by a plurality of joint units (for example, the arm unit 420 illustrated in FIG. 2 in the present embodiment), for converting motion purposes regarding various dimensions in various operation spaces into torques to be caused in the plurality of joint units in consideration of various constraint conditions.

The operation space is an important concept in force control of a device. The operation space is a space for describing a relationship between force acting on the multilink structure and acceleration of the multilink structure. When the drive control of the multilink structure is performed not by position control but by force control, the concept of the operation space is necessary in a case of using a contact between the multilink structure and an environment as a constraint condition. The operation space is, for example, a joint space, a Cartesian space, a momentum space, or the like, which is a space to which the multilink structure belongs.

The motion purpose represents a target value in the drive control of the multilink structure, and is, for example, a target value of a position, a speed, an acceleration, a force, an impedance, or the like of the multilink structure to be achieved by the drive control.

The constraint condition is a constraint condition regarding the position, speed, acceleration, force, or the like of the multilink structure, which is determined according to a shape or a structure of the multilink structure, an environment around the multilink structure, setting by the user, and the like. For example, the constraint condition includes information regarding a generated force, a priority, presence/absence of a non-drive joint, a vertical reaction force, a friction weight, a support polygon, and the like.

In the generalized dynamics, to establish both stability of numerical calculation and real time processing efficiency, an arithmetic algorithm includes a virtual force determination process (virtual force calculation processing) as a first stage and a real force conversion process (real force calculation processing) as a second stage. In the virtual force calculation processing as the first stage, a virtual force that is a virtual force necessary for achievement of each motion purpose and acting on the operation space is determined while considering the priority of the motion purpose and a maximum value of the virtual force. In the real force calculation processing as the second stage, the above-obtained virtual force is converted into a real force realizable in the actual configuration of the multilink structure, such as a joint force or an external force, while considering the constraints regarding the non-drive joint, the vertical reaction force, the friction weight, the support polygon, and the like. Hereinafter, the virtual force calculation processing and the real force calculation processing will be described in detail. Note that, in the description of the virtual force calculation processing and the real force calculation processing below and the ideal joint control to be described below, description may be performed using the configuration of the arm unit 420 of the support arm device 400 according to the present embodiment illustrated in FIG. 2 as a specific example, in order to facilitate the understanding.

(2-2-1. Virtual Force Calculation Processing)

A vector configured by a certain physical quantity at each joint unit of the multilink structure is called generalized variable q (also referred to as a joint value q or a joint space q). An operation space x is defined by the following mathematical expression (1) using a time derivative value of the generalized variable q and the Jacobian J.

[Math. 1]

$$\dot{x} = J\dot{q} \qquad (1)$$

In the present embodiment, for example, q represents a rotation angle of the joint units 421a to 421f of the arm unit 420. An equation of motion regarding the operation space x is described by the following mathematical expression (2).

[Math. 2]

$$\ddot{x} = \Lambda^{-1} f + c \qquad (2)$$

Here, f represents a force acting on the operation space x. Furthermore, $\Lambda^{-1}$ represents an operation space inertia inverse matrix, and c is called operation space bias acceleration, which are respectively expressed by the following mathematical expressions (3) and (4).

[Math. 3]

$$\Lambda^{-1} = JH^{-1}J^T \qquad (3)$$

$$c = JH^{-1}(\tau - b) + \dot{J}\dot{q} \qquad (4)$$

Note that H represents a joint space inertia matrix, τ represents a joint force corresponding to the joint value q (for example, the generated torque in the joint units 421a to 421f), and b represents gravity, a Coriolis force, and a centrifugal force. In the generalized inverse dynamics, it is known that the motion purpose of the position and speed regarding the operation space x can be expressed as an acceleration of the operation space x. At this time, the virtual force $f_v$ to act on the operation space x to realize an operation space acceleration that is a target value given as the motion purpose can be obtained by solving a kind of linear complementary problem (LCP) as in the mathematical expression (5) below according to the above mathematical expression (1).

[Math. 4]

$$w + \ddot{x} = \Lambda^{-1} f_v + c \qquad (5)$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ respectively represent a negative lower limit value (including $-\infty$) of an i-th component of $f_v$ and a positive upper limit value (including $+\infty$) of the i-th component of $f_v$. The above LCP can be solved using, for example, an iterative method, a pivot method, a method applying robust acceleration control, or the like.

Note that the operation space inertia inverse matrix $\Lambda^{-1}$ and the bias acceleration c have a large calculation cost when calculated according to the mathematical expressions (3) and (4) that are defining mathematical expressions. Therefore, a method of calculating the processing of calculating the operation space inertia inverse matrix $\Lambda^{-1}$ at a high speed by applying a quasi-dynamics operation (FWD) for obtaining a generalized acceleration (joint acceleration) from the generalized force (joint force τ) of the multilink structure has been proposed. Specifically, the operation space inertia inverse matrix $\Lambda^{-1}$ and the bias acceleration c can be obtained from information regarding forces acting on the multilink structure (for example, of the arm unit 420 and the joint units 421a to 421f), such as the joint space q, the joint force τ, and the gravity g by using the forward dynamics arithmetic operation FWD. The operation space inertia inverse matrix $\Lambda^{-1}$ can be calculated with a calculation amount of O (N) with respect to the number N of the joint units by applying the forward dynamics arithmetic operation FWD regarding the operation space.

Here, as a setting example of the motion purpose, a condition for achieving the target value (expressed by adding a superscript bar to second order differentiation of x) of the operation space acceleration with a virtual force $f_{vi}$ equal to or smaller than an absolute value $F_i$ can be expressed by the following mathematical expression (6).

[Math. 5]

$$L_i = -F_i,$$

$$U_i = F_i,$$

$$\ddot{x}_i = \bar{\ddot{x}}_i \qquad (6)$$

Furthermore, as described above, the motion purpose regarding the position and speed of the operation space x can be expressed as the target value of the operation space acceleration, and is specifically expressed by the following mathematical expression (7) (the target value of the position and speed of the operation space x is expressed by x and adding the superscript bar to first order differentiation of x).

[Math. 6]

$$\bar{\ddot{x}}_i = K_p(\bar{x}_i - x_i) + K_v(\bar{\dot{x}}_i - \dot{x}_i) \qquad (7)$$

In addition, by use of a concept of decomposition operation space, the motion purpose regarding an operation space (momentum, Cartesian relative coordinates, interlocking joint, or the like) expressed by a linear sum of other operation spaces can be set. Note that it is necessary to give priority to competing motion purposes. The above LCP can be solved for each priority in ascending order from a low priority, and the virtual force obtained by the LCP in the previous stage can be made to act as a known external force of the LCP in the next stage.

(2-2-2. Real Force Calculation Processing)

In the real force calculation processing as the second stage of the generalized inverse dynamics, processing of replacing the virtual force $f_v$ obtained in the above (2-2-1. Virtual Force Determination Process) with real joint force and external force is performed. A condition for realizing the generalized force $\tau_v = J_v^T f_v$ by the virtual force with a generated torque $\tau_a$ generated in the joint unit and an external force $f_e$ is expressed by the following mathematical expression (8).

[Math. 7]

$$\begin{bmatrix} J_{vu}^T \\ J_{va}^T \end{bmatrix} (f_v - \Delta f_v) = \begin{bmatrix} J_{eu}^T \\ J_{ea}^T \end{bmatrix} f_e + \begin{bmatrix} 0 \\ \tau_a \end{bmatrix} \qquad (8)$$

Here, the suffix a represents a set of drive joint units (drive joint set), and the suffix u represents a set of non-drive joint units (non-drive joint set). In other words, the upper part of the above mathematical expression (8) represents balance of the forces of the space (non-drive joint space) by the non-drive joint units, and the lower part represents balance of the forces of the space (drive joint space) by the drive joint units. $J_{vu}$ and $J_{va}$ are respectively a non-drive joint component and a drive joint component of the Jacobian regarding the operation space where the virtual force $f_v$ acts. $J_{eu}$ and $J_{ea}$ are a non-drive joint component and a drive joint component of the Jacobian regarding the operation space where the external force $f_e$ acts. $\Delta f_v$ represents an unrealizable component with the real force, of the virtual force $f_v$.

The upper part of the mathematical expression (8) is undefined. For example, $f_e$ and $\Delta f_v$ can be obtained by solving a quadratic programming problem (QP) as described in the following mathematical expression (9).

[Math. 8]

$$\min \tfrac{1}{2} \varepsilon^T Q_1 \varepsilon + \tfrac{1}{2} \xi^T Q_2 \xi$$

$$\text{s.t.} U\xi \geq v \qquad (9)$$

Here, ε is a difference between both sides of the upper part of the mathematical expression (8), and represents an mathematical expression error of the mathematical expression (8). ξ is a connected vector of $f_e$ and $\Delta f_v$ and represents a variable vector. $Q_1$ and $Q_2$ are positive definite symmetric matrices that represent weights at minimization. Furthermore, inequality constraint of the mathematical expression (9) is used to express the constraint condition regarding the external force such as the vertical reaction force, friction cone, maximum value of the external force, or support polygon. For example, the inequality constraint regarding a rectangular support polygon is expressed by the following mathematical expression (10).

[Math. 9]

$$|F_x| \leq \mu_t F_z,$$
$$|F_y| \leq \mu_t F_z,$$
$$F_z \geq 0,$$
$$|M_x| \leq d_y F_z,$$
$$|M_y| \leq d_x F_z,$$
$$|M_z| \leq \mu_r F_z \qquad (10)$$

Here, z represents a normal direction of a contact surface, and x and y represent orthogonal two-tangent directions perpendicular to z. $(F_x, F_y, F_z)$ and $(M_x, M_y, M_z)$ represent an external force and an external force moment acting on a contact point. $\mu_t$ and $\mu_r$ are friction coefficients regarding translation and rotation, respectively. $(d_x, d_y)$ represents the size of the support polygon.

From the above mathematical expressions (9) and (10), solutions $f_e$ and $\Delta f_v$ of a minimum norm or a minimum error are obtained. By substituting $f_e$ and $\Delta f_v$ obtained from the above mathematical expression (9) into the lower part of the above mathematical expression (8), the joint force $\tau_a$ necessary for realizing the motion purpose can be obtained.

In a case of a system where a base is fixed and there is no non-drive joint, all virtual forces can be replaced only with the joint force, and $f_e=0$ and $\Delta f_v=0$ can be set in the above mathematical expression (8). In this case, the following mathematical expression (11) can be obtained for the joint force $\tau_a$ from the lower part of the above mathematical expression (8).

[Math. 10]

$$\tau_a = J_{va}^T f_v \qquad (11)$$

The whole body coordination control using the generalized inverse dynamics according to the present embodiment has been described. By sequentially performing the virtual force calculation processing and the real force calculation processing as described above, the joint force $\tau_a$ for achieving a desired motion purpose can be obtained. In other words, conversely speaking, by reflecting the calculated joint force $\tau_a$ in a theoretical model in the motion of the joint units 421a to 421f, the joint units 421a to 421f are driven to achieve the desired motion purpose.

Note that, regarding the whole body coordination control using the generalized inverse dynamics described so far, in particular, details of the process of deriving the virtual force $f_v$, the method of solving the LCP to obtain the virtual force $f_v$, the solution of the QP problem, and the like, reference can be made to Japanese Patent Application Laid-Open No. 2009-95959 and Japanese Patent Application Laid-Open No. 2010-188471, which are prior patent applications filed by the present applicant, for example.

[2-3. Ideal Joint Control]

Next, the ideal joint control according to the present embodiment will be described. The motion of each of the joint units 421a to 421f is modeled by the mathematical expression of motion of the second order lag system of the following mathematical expression (12).

[Math. 11]

$$I_a \ddot{q} = \tau_a + \tau_e - \nu_a \dot{q} \qquad (12)$$

Here, $I_a$ represents moment of inertia (inertia) at the joint unit, $\tau_a$ represents the generated torque of the joint units 421a to 421f, $\tau_e$ represents external torque acting on each of the joint units 421a to 421f from the outside, and $\nu_e$ represents a viscous drag coefficient in each of the joint units 421a to 421f. The above mathematical expression (12) can also be said to be a theoretical model that represents the motion of the actuators in the joint units 421a to 421f.

$\tau_a$ that is the real force to act on each of the joint units 421a to 421f for realizing the motion purpose can be calculated using the motion purpose and the constraint condition by the arithmetic operation using the generalized inverse dynamics described in [2-2. Generalized Inverse Dynamics] above. Therefore, ideally, by applying each calculated $\tau_a$ to the above mathematical expression (12), a response according to the theoretical model illustrated in the above mathematical expression (12) is realized, in other words, the desired motion purpose should be achieved.

However, in practice, errors (modeling errors) may occur between the motions of the joint units 421a to 421f and the theoretical model as illustrated in the above mathematical expression (12), due to the influence of various types of disturbance. The modeling errors can be roughly classified into those due to mass property such as weight, center of gravity, inertia tensor of the multilink structure, and those due to friction, inertia, and the like inside joint units 421a to 421f. Among them, the modeling errors due to the former mass property can be relatively easily reduced at the time of constructing the theoretical model by improving the accuracy of computer aided design (CAD) data and applying an identification method.

Meanwhile, the modeling errors due to the latter friction, inertia, and the like inside the joint units 421a to 421f are caused by phenomena that are difficult to model, such as friction in a speed reducer 426 of the joint units 421a to 421f, for example, and a modeling error that is not ignored may remain during theoretical model construction. Furthermore, there is a possibility that an error occurs between the values of the inertia $I_a$ and the viscous drag coefficient $\nu_e$ in the above mathematical expression (12) and the values in the actual joint units 421a to 421f. These errors that are difficult to model can become the disturbance in the drive control of the joint units 421a to 421f. Therefore, in practice, the motions of the joint units 421a to 421f may not respond according to the theoretical model illustrated in the above mathematical expression (12), due to the influence of such disturbance. Therefore, even when the real force $\tau_a$, which is a joint force calculated by the generalized inverse dynamics, is applied, there may be a case where the motion purpose that is the control target is not achieved.

Therefore, in the present embodiment, correcting the responses of the joint units 421a to 421f so as to perform ideal responses according to the theoretical model illustrated in the above mathematical expression (12), by adding an active control system to each of the joint units 421a to 421f, is considered. At this time, for example, as described in Patent Document 1, by using the torque sensor, not only performing friction compensation-type torque control but also performing an ideal response according to theoretical values for the required generated torque $\tau_a$ and the external torque $\tau_e$ to reach the inertia $I_a$ and the viscous drag coefficient $\nu_a$ is assumed. Note that, in the following description, the generated torque $\tau_a$ is also referred to as a command torque or a control value in the sense of a command value to the joint units 421a to 421f in the whole body coordination control.

Figure 3:
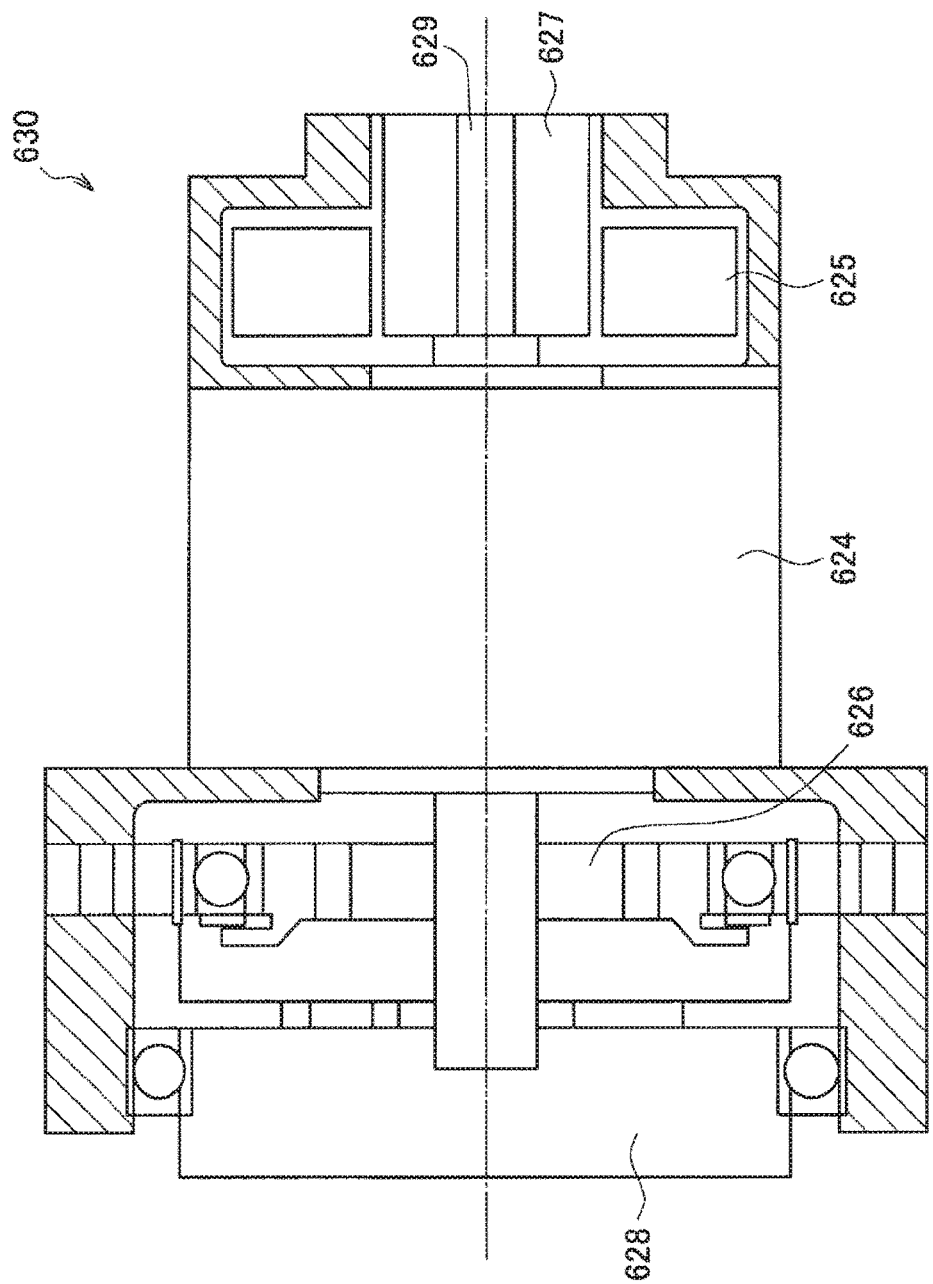
FIG. 3 is a cross-sectional view schematically illustrating a state in which an actuator including a torque sensor is cut along a cross section passing through a rotation axis.

Here, a configuration of an actuator including a torque sensor as described in Patent Document 1 will be described with reference to FIG. 3. FIG. 3 is a cross-sectional view schematically illustrating a state in which the actuator including the torque sensor is cut along a cross section passing through a rotation axis. An actuator 630 including the torque sensor illustrated in FIG. 3 can also be applied to a part of the joint units 421a to 421f according to the present embodiment.

Note that, as described above, in the present embodiment, the drive of the joint units 421a to 421f is controlled by the ideal joint control. Therefore, the actuator 630 illustrated in FIG. 3 is configured to be able to perform drive corresponding to the ideal joint control. Specifically, the actuator 630 is configured to be able to adjust the rotation angle and a torque associated with the rotation drive in the joint units 421a to 421f. Furthermore, the actuator 630 is configured to be able to arbitrarily adjust the viscous drag coefficient for rotational motion and can realize an easily rotatable state (in other words, a state of easily manually moving the arm unit 420) and a less easily rotatable state (in other words, a state of less easily manually moving the arm unit 420) with respect to a force applied from an outside.

Referring to FIG. 3, the actuator 630 includes a motor 624, a motor driver 625, a speed reducer 626, an encoder 627, a torque sensor 628, and a drive shaft 629. As illustrated in FIG. 3, the encoder 627, the motor 624, the speed reducer 626, the torque sensor 628 are connected in series to the drive shaft 629 in this order.

The motor 624 is a prime mover in the actuator 630, and rotates the drive shaft 629 around the axis. For example, the motor 624 is an electric motor such as a brushless DC motor. In the present embodiment, the rotation drive of the motor 624 is controlled by supplying a current.

The motor driver 625 is a driver circuit (driver integrated circuit (IC)) that supplies a current to the motor 624 to rotationally drive the motor 624, and can control the number of rotations of the motor 624 by adjusting a current amount to be supplied to the motor 624. Furthermore, the motor driver 625 can adjust the viscous drag coefficient for rotational motion of the actuator 630 by adjusting the current amount to be supplied to the motor 624.

The speed reducer 626 is connected to the drive shaft 629 and reduces a rotational speed of the drive shaft 629 caused by the motor 624 at a predetermined reduction ratio to generate a rotational drive force (in other words, torque) having a predetermined value. As the speed reducer 626, a backlashless-type high performance speed reducer is used. For example, the speed reducer 626 may be a harmonic drive (registered trademark). The torque generated by the speed reducer 626 is transmitted to a subsequent output member (not illustrated, for example, a connecting member of the links 422a to 422c, the imaging unit 423, or the like) via the torque sensor 628 connected to an output shape of the speed reducer 626.

The encoder 627 is connected to the drive shaft 629 and detects the number of rotations of the drive shaft 629. Information of the rotation angle, rotation angular speed, rotation angular acceleration, and the like of the joint units 421a to 421f can be obtained on the basis of the relationship between the number of rotations of the drive shaft 629 detected by the encoder 627 and the reduction ratio of the speed reducer 626.

The torque sensor 628 is connected to the output shaft of the speed reducer 626, and detects the torque generated by the speed reducer 626, in other words, the torque output by the actuator 630.

As described above, the actuator 630 can adjust the number of rotations of the motor 624 by adjusting the current amount to be supplied to the motor 624. Here, the reduction ratio in the speed reducer 626 may be appropriately set according to the use of the support arm device 400. Therefore, the command torque can be controlled by appropriately adjusting the number of rotations of the motor 624 according to the reduction ratio of the speed reducer 626. Furthermore, in the actuator 630, the information of the rotation angle, rotation angular speed, rotation angular acceleration, and the like of the joint units 421a to 421f can be obtained on the basis of the number of rotations of the drive shaft 629 detected by the encoder 627, and the command torque in the joint units 421a to 421f can be detected by the torque sensor 628.

Furthermore, the torque sensor 628 can detect not only the command torque of the actuator 630 but also the external torque applied from the outside. Therefore, the motor driver 625 can adjust the viscous drag coefficient for rotational motion as described above by adjusting the current amount to be supplied to the motor 624 on the basis of the external torque detected by the torque sensor 628, and the easily rotatable state or the less easily rotatable state with respect to the force applied from the outside can be realized, for example.

Note that, in the present embodiment, control of the drive of the joint units 421a to 421f of the support arm device 400 to perform ideal responses as described in the above mathematical expression (12) is called ideal joint control. Here, in the following description, an actuator controlled to be driven by the ideal joint control is also referred to as a virtualized actuator (VA) because of performing an ideal response. Hereinafter, the ideal joint control based on the external torque detected by the torque sensor 628 will be described with reference to FIG. 4.

Figure 4:
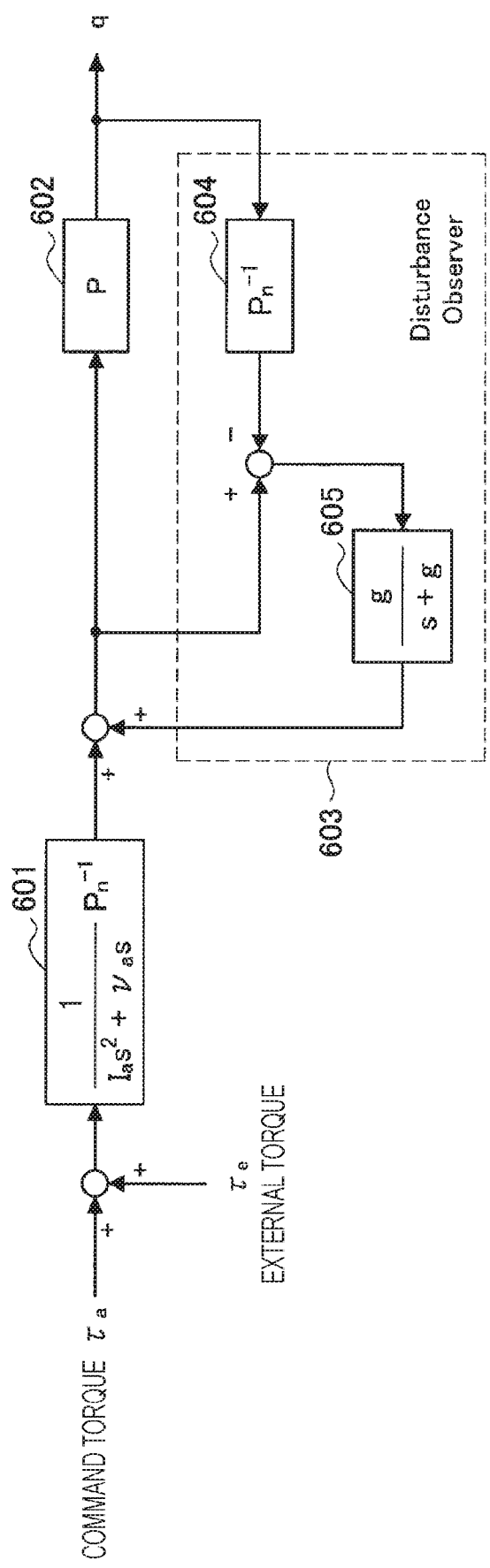
FIG. 4 is an explanatory diagram for describing ideal joint control based on an external torque detected by a torque sensor.

FIG. 4 is an explanatory diagram for describing the ideal joint control based on the external torque detected by the torque sensor. Note that FIG. 4 schematically illustrates a conceptual arithmetic unit that performs various arithmetic operations regarding the ideal joint control in blocks. Note that the nominal model of P in FIG. 4 is $P_n=1/(J_n S^2)$.

A block 601 represents an arithmetic unit that performs an arithmetic operation according to an ideal joint model of the joint units 421a to 421f illustrated in the above mathematical expression (12). The block 601 can calculate and output a rotation angular acceleration target value (a second order differentiation of a rotation angle target value $q^{ref}$) described on the left side of the above mathematical expression (12), using the command torque $\tau_a$, the external torque $\tau_e$, and the rotation angular speed (first order differentiation of the rotation angle q) as inputs.

As illustrated in FIG. 4, the command torque $\tau_a$ calculated by the method described in [2-2. Generalized Inverse Dynamics] above and the external torque $\tau_e$ measured by the torque sensor 628 are input to the block 601. Furthermore, when the rotation angle q measured by the encoder 627 is input to a block 602 that performs a differential operation, the rotation angular speed (the first order differentiation of the rotation angle q) is calculated. When the rotation angular speed calculated as described above is input to the block 601 in addition to the command torque $\tau_a$ and the external torque $\tau_e$, the rotation angular acceleration target value is calculated by the block 601.

Furthermore, the block 601 calculates a torque generated in the actuator 630 on the basis of the rotation angular acceleration of the actuator 630. Specifically, the block 601 can obtain a torque target value $\tau^{ref}$ by multiplying the rotation angular acceleration target value by nominal inertia $J_n$ in the actuator 630. In the ideal response, the desired motion purpose should be achieved by causing the actuator 630 to generate the torque target value $\tau^{ref}$. However, as described above, there is a case where the influence of the disturbance or the like occurs in the actual response. Therefore, in the present embodiment, the disturbance observer 603 calculates a disturbance estimation value $\tau_d$ and corrects the torque target value $\tau^{ref}$ using the disturbance estimation value $\tau_d$.

A configuration of the disturbance observer 603 will be described. As illustrated in FIG. 4, the disturbance observer 603 calculates the disturbance estimation value $\tau_d$ on the basis of the command torque $\tau_a$ and the rotation angular speed output from the rotation angle q measured by the encoder 627. Here, the command torque $\tau_a$ is a torque value to be finally generated in the actuator 630 after the influence of disturbance is corrected. For example, in a case where the disturbance estimation value $\tau_d$ is not calculated, the command torque $\tau_a$ becomes the torque target value $\tau^{ref}$.

The disturbance observer 603 includes a block 604 and a block 605. The block 604 represents an arithmetic unit that calculates a torque generated in the actuator 630 on the basis of the rotation angular speed of the actuator 630. Specifically, the rotation angular speed calculated by the block 602 from the rotation angle q measured by the encoder 627 is input to the block 604. The block 604 obtains the rotation angular acceleration by performing an arithmetic operation represented by a transfer function $J_n s$, in other words, by differentiating the rotation angular speed, and further multiplies the calculated rotation angular acceleration by the nominal inertia $J_n$, thereby calculating an estimation value (torque estimation value) of the torque actually acting on the actuator 630.

In the disturbance observer 603, the difference between the torque estimation value and the command torque $\tau_a$ is obtained, whereby the disturbance estimation value $\tau_d$ that is the value of the torque due to the disturbance is estimated. Specifically, the disturbance estimation value $\tau_d$ may be a difference between the command torque $\tau_a$ in the control of the preceding cycle and the torque estimation value in the current control. Since the torque estimation value calculated by the block 604 is based on the actual measurement value, and the command torque $\tau_a$ calculated by the block 601 is based on the ideal theoretical model of the joint units 421a to 421f illustrated in the block 631, the influence of the disturbance, which is not considered in the theoretical model, can be estimated by taking the difference between the torque estimation value and the command torque $\tau_a$.

Furthermore, the disturbance observer 603 is provided with a low pass filter (LPF) illustrated in a block 605 to prevent system divergence. The block 605 outputs only a low frequency component to the input value by performing an arithmetic operation represented by a transfer function g/(s+g) to stabilize the system. The difference value between the torque estimation value calculated by the block 604 and the torque command value $\tau_a$ is input to the block 605, and a low frequency component of the difference value is calculated as the disturbance estimation value $\tau_d$.

Feedforward control to add the disturbance estimation value $\tau_d$ calculated by the disturbance observer 603 to the torque target value $\tau^{ref}$ is performed as described above, so that the command torque $\tau_a$ that is the torque value to be finally generated in the actuator 630 is calculated. Then, the actuator 630 is driven on the basis of the command torque $\tau_a$. Specifically, the command torque $\tau_a$ is converted into a corresponding current value (current command value), and the current command value is applied to the motor 624, so that the actuator 630 is driven.

The ideal joint control based on the external torque detected by the torque sensor has been described above with reference to FIG. 4. With the above-described configuration, the response of the actuator 630 can be made to follow the target value even in a case where there is a disturbance component such as friction in the drive control of the joint units 421a to 421f. Furthermore, with regard to the drive control of the joint units 421a to 421f, an ideal response according to the inertia $I_a$ and the viscous drag coefficient va assumed by the theoretical model can be made.

However, in a configuration using a torque sensor, an external force acting on an actuator or the like can be detected with high accuracy, but manufacturing, assembly, management, and the like are generally costly. Furthermore, the torque sensor may be subject to operation restrictions and environmental restrictions. For example, since a torque sensor such as a six-axis force sensor can detect only an external force acting on a component to be arranged, the torque sensor cannot detect an external force acting on another component. Furthermore, the torque sensor may not be arranged in an environment such as under a high temperature. For this reason, in a torque control-type device based on external force, a technique capable of realizing highly accurate force control has been demanded even in a case where a torque sensor is not used.

From the background as described above, the present inventors have arrived at an idea of a control device 20 of the present embodiment that realizes torque control based on an estimated external force. More specifically, the control device 20 according to the present embodiment is characterized in including an external force estimation unit 260 that estimates an external force acting on the joint units 421a to 421f of the support arm device 400 on the basis of a drive characteristic of the actuator, and controls the drive of the joint units 421a to 421f on the basis of the external torque estimated by the external force estimation unit 260.

According to the control device 20 of the present embodiment, the external torque acting on the joint units 421a to 421f can be detected with high accuracy without using a torque sensor, and more flexible force control in which the operation restrictions and environmental restrictions are eliminated can be realized. Furthermore, according to the control device 20 of the present embodiment, provision of the torque sensor as a physical configuration is not necessary. Therefore, the cost related to the manufacturing and maintenance of the torque sensor can be effectively reduced, and the total cost for introducing and operating the support arm device 400 can be reduced.

Figure 5:
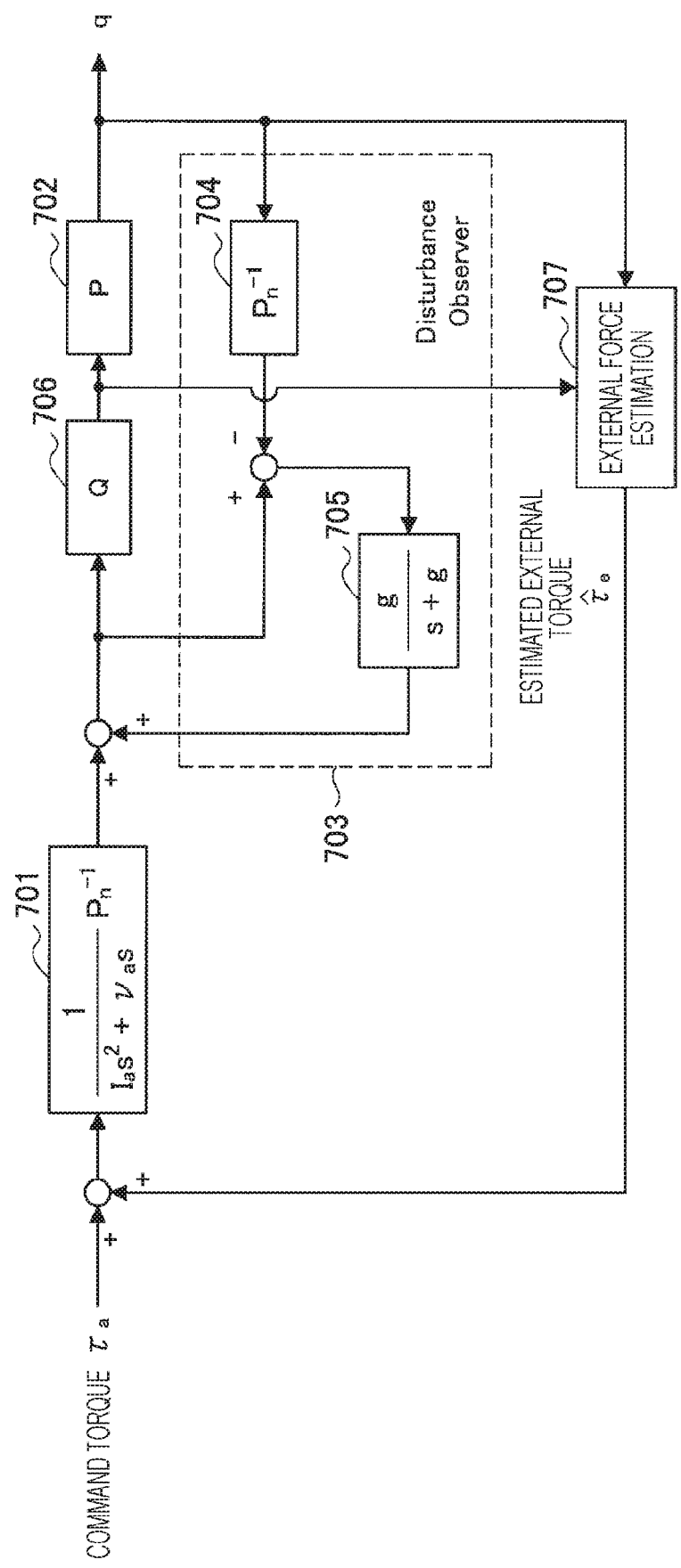
FIG. 5 is an explanatory diagram for describing ideal joint control based on external force estimation according to an embodiment of the present disclosure.

Hereinafter, the ideal joint control by the control device 20 according to the present embodiment will be described. FIG. 5 is an explanatory diagram for describing the ideal joint control based on external force estimation according to the present embodiment. Note that FIG. 5 schematically illustrates a conceptual arithmetic unit that performs various arithmetic operations regarding the ideal joint control based on external force estimation in blocks. Note that the nominal model of P in FIG. 5 is $P_n = 1/(J_n S^2)$. Furthermore, in the following description, differences from the block diagram based on the torque sensor illustrated in FIG. 4 will be mainly described, and detailed description regarding common configurations will be omitted.

A block 701 represents an arithmetic unit that performs an arithmetic operation according to an ideal joint model of the joint units 421a to 421f. The block 701 is different from the block 601 illustrated in FIG. 4, and performs an arithmetic operation using an estimated external torque $\hat{\tau}_e$ estimated by a block 707 as an input, instead of the external torque $\tau_e$ detected by the torque sensor.

At this time, the block 707 estimates the estimated external torque $\hat{\tau}_e$ on the basis of a characteristic of the motor applied to the actuator. A block 702 in FIG. 5 represents an arithmetic unit that performs an arithmetic operation depending on the characteristic of the motor applied to the actuator. As described above, in the ideal joint control according to the present embodiment, the arithmetic operation based on a characteristic of an applied motor is performed, whereby various motors can be coped with and the estimated external torque $\hat{\tau}_e$ can be estimated with high accuracy.

Hereinafter, details of the ideal joint control according to the type of a motor by the control device 20 according to the present embodiment will be described. Here, examples of the motor include an electromagnetic motor, an ultrasonic motor, and the like. First, the ideal joint control regarding an actuator including an electromagnetic motor will be described.

Figure 6:
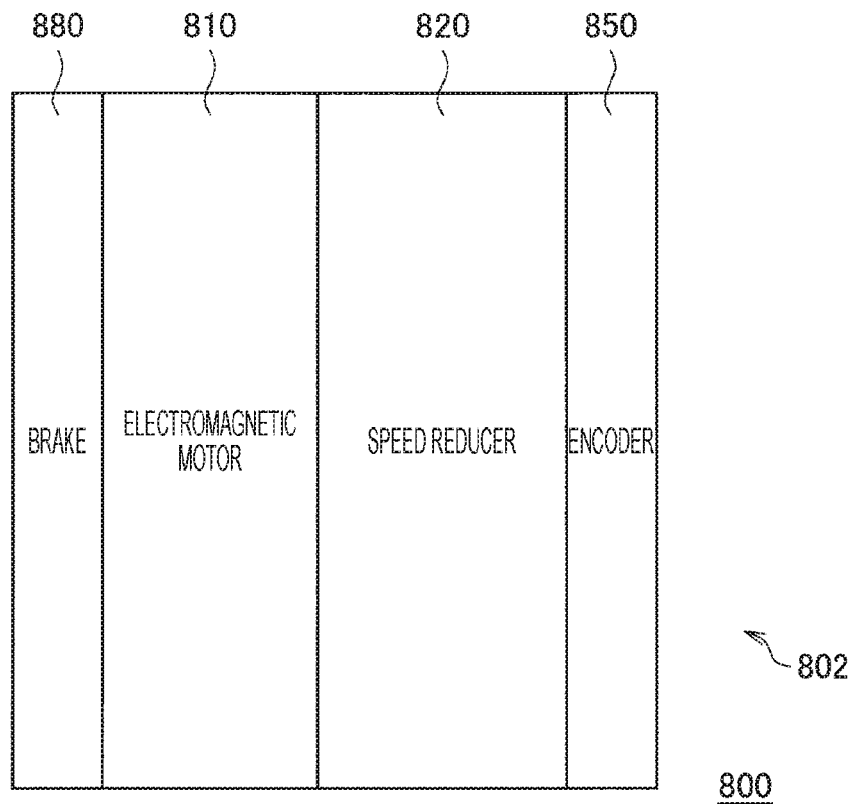
FIG. 6 is a diagram schematically illustrating a schematic configuration of an actuator including an electromagnetic motor according to the embodiment.

FIG. 6 is a diagram schematically illustrating a schematic configuration 802 of an actuator 800 including an electromagnetic motor 810. As illustrated in FIG. 6, the actuator 800 of the present embodiment includes the electromagnetic motor 810, a speed reducer 820, an encoder 850, and a brake 880 as main configuration elements.

Figure 7:
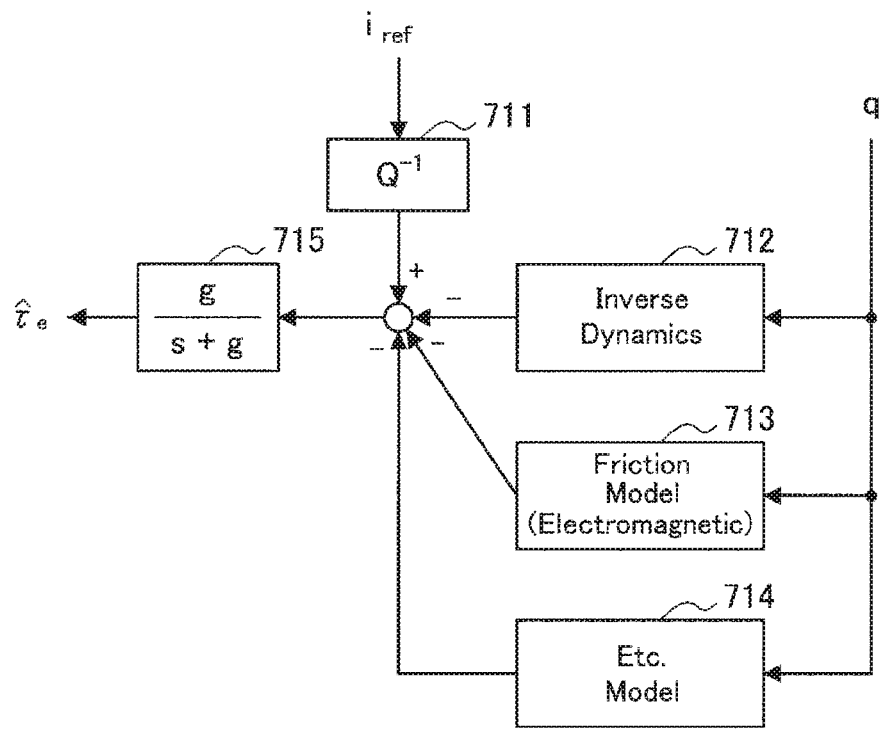
FIG. 7 is a diagram for describing external force estimation of a case where the actuator including the electromagnetic motor according to the embodiment is applied.

Furthermore, FIG. 7 is a diagram for describing external force estimation in a case where the actuator 800 including the electromagnetic motor 810 is applied. FIG. 7 schematically illustrates a conceptual arithmetic unit that performs various arithmetic operations according to the electromagnetic motor 810 in blocks.

In the case where the electromagnetic motor 810 is used for the drive of the joint units 421a to 421f, the control device 20 according to the present embodiment can estimate the estimated external torque $\hat{\tau}_e$ on the basis of a current command torque $\tau_{i\_ref}$ using a current value firer and a motion estimation torque $\tau_{mt}$ using an encoder value q. In other words, the control device 20 according to the present embodiment realizes the ideal joint control by using the following mathematical expression (13) instead of the above mathematical expression (12).

[Math. 12]

$$I_a \ddot{q} = \tau_a + \hat{\tau}_e - \nu_a \dot{q} = \tau_a + (\tau_{i\_ref} - \tau_{mt}) - \nu_a \dot{q} \quad (13)$$

A block 711 in FIG. 7 is an arithmetic unit that calculates a torque value according to the type of the motor. In the case where the electromagnetic motor 810 is used for the drive of the joint units 421a to 421f, the block 711 outputs the current command torque $\tau_{i\_ref}$ on the basis of the input current value $i_{ref}$. Here, Q illustrated in FIG. 7 may be Q=1/$K_t$. The block 711 can calculate the current command torque $\tau_{i\_ref}$ by the following mathematical expression (14). Note that $K_t$ represents a torque constant.

[Math. 13]

$$\tau_{i\_ref} = K_t i_{ref} \quad (14)$$

Furthermore, the control device 20 according to the present embodiment calculates the motion estimation torque $\tau_{mt}$ by the following mathematical expression (15) on the basis of the characteristic of the electromagnetic motor 810.

[Math. 14]

$$\tau_{mt} = M(q)\ddot{q} + c(q,\dot{q}) + g(q) + h(\dot{q}) + k(q,\dot{q},\ddot{q}) \quad (15)$$

M, c, and g in the above mathematical expression (15) represent an inertia term, a velocity term, and a gravity term based on design information of the electromagnetic motor 810, respectively. A block 712 illustrated in FIG. 7 is an arithmetic block that outputs the inertia term, the velocity term, and the gravity term on the basis of the design information of the motor.

Furthermore, h and k in the above mathematical expression (15) represent a friction torque and an internal consumption torque, respectively. A block 713 illustrated in FIG. 7 is an arithmetic unit that calculates the friction torque, and a block 714 is an arithmetic unit that calculates the internal consumption torque such as a distortion torque and a torsion torque. At this time, the blocks 713 and 714 are characterized in using a model identification result for the calculation of the friction torque and the internal consumption torque that cannot be calculated from the design information.

Figure 8:
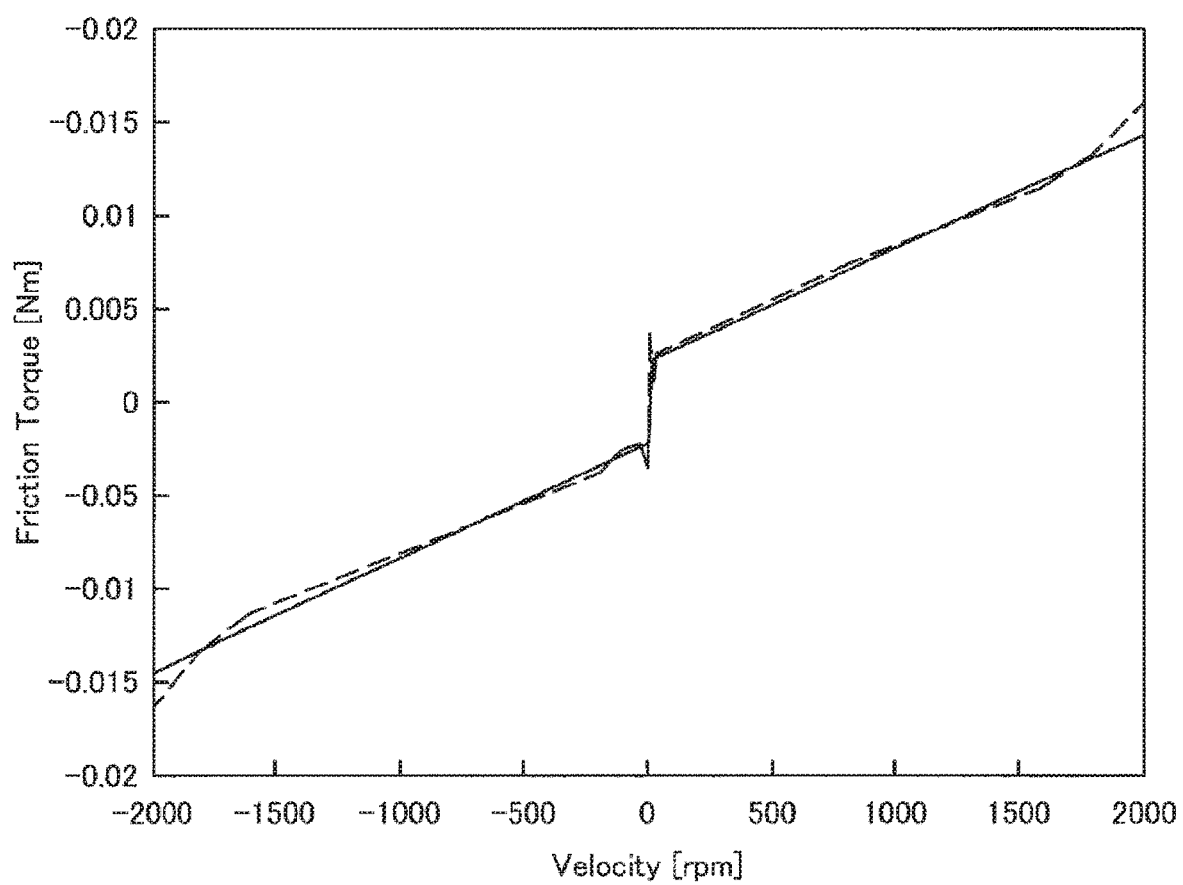
FIG. 8 is a graph for describing model identification using measurement tests of static friction and dynamic friction according to a speed reducer according to the embodiment.

FIG. 8 is a graph for describing model identification using measurement tests of static friction and dynamic friction according to the speed reducer 820. In FIG. 8, the measured static friction torque and dynamic friction torque of the speed reducer 820 are illustrated by the dotted line, and the friction torque modeled on the basis of measurement values is illustrated by the solid line. At this time, the following mathematical expression (16) may be used for the modeling the friction torque, for example.

[Math. 15]

$$h(\dot{q}) = F_c \cdot \text{sgn}(\dot{q}) + D\dot{q} \quad (16)$$

Note that, in the above mathematical expression (16), Fc represents a static friction coefficient, D represents a viscous friction coefficient, and sgn represents a sign function corresponding to the rotation angular speed. Furthermore, the above mathematical expression (16) is merely an example, and the model mathematical expression of the friction torque according to the present embodiment may be higher order or a continuous function.

As described above, the control device 20 according to the present embodiment enables the estimation of the external torque with high accuracy by calculating various values according to the characteristics of the electromagnetic motor 810, and can realize the ideal joint control without using a torque sensor. Note that a block 715 in FIG. 7 represents a low-pass filter.

Figure 9:
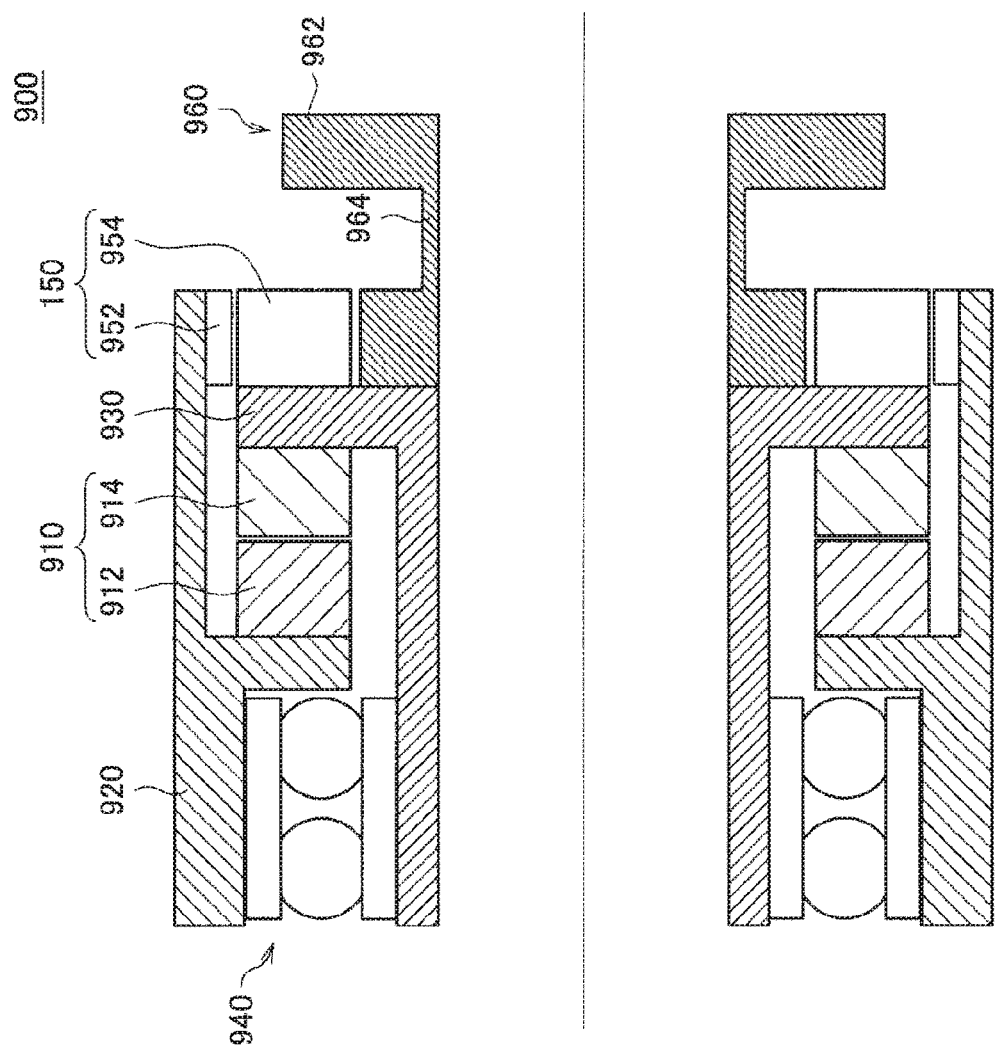
FIG. 9 is a cross-sectional view illustrating a configuration example of an actuator including an ultrasonic motor according to the embodiment.

First, the ideal joint control regarding an actuator including an ultrasonic motor will be described. First, a configuration example of an actuator 900 including an ultrasonic motor will be described. FIG. 9 is a cross-sectional view illustrating a configuration example of the actuator 900 according to the present embodiment. The actuator 900 includes an ultrasonic motor 910, a fixed frame 920, a rotating frame 930, a bearing 940, an encoder 950, and an output frame 960. The ultrasonic motor 910, the fixed frame 920, the rotating frame 930, the bearing 940, the encoder 950, and the output frame 960 are all configured in a hollow ring shape.

The fixed frame 920 is fixed to one of two members that relatively rotate in the joint units 421a to 421f. The ultrasonic motor 910 includes a stator 912 and a rotor 914. The stator 912 is equipped with a piezoelectric element (piezo element) that generates ultrasonic vibration (not illustrated). The rotor 914 is pressed against a vibration surface of the stator 912 and rotates by the ultrasonic vibration of the stator 912. The rotating frame 930 is fixed to the rotor 914 and rotates together with the rotor 914. The bearing 940 is provided between the fixed frame 920 and the rotating frame 930, and is configured such that the rotating frame 930 rotates with respect to the fixed frame 920 via the bearing 940.

The output frame 960 is fixed to the rotating frame 930 and rotates together with the rotating frame 930. An end portion 162 of the output frame 960 opposite to the rotating frame 930 is fixed to the other of the two members that relatively rotate in the joint units 421a to 421f. Furthermore, the output frame 960 is provided with a thin-walled portion 964 having a thickness in a radial direction thinner than a periphery.

The encoder 950 includes a detection unit 952 and a rotor 954, and detects a rotation angle of the rotor 954 as the detection unit 952 detects the rotation of the rotor 954.

Figure 10:
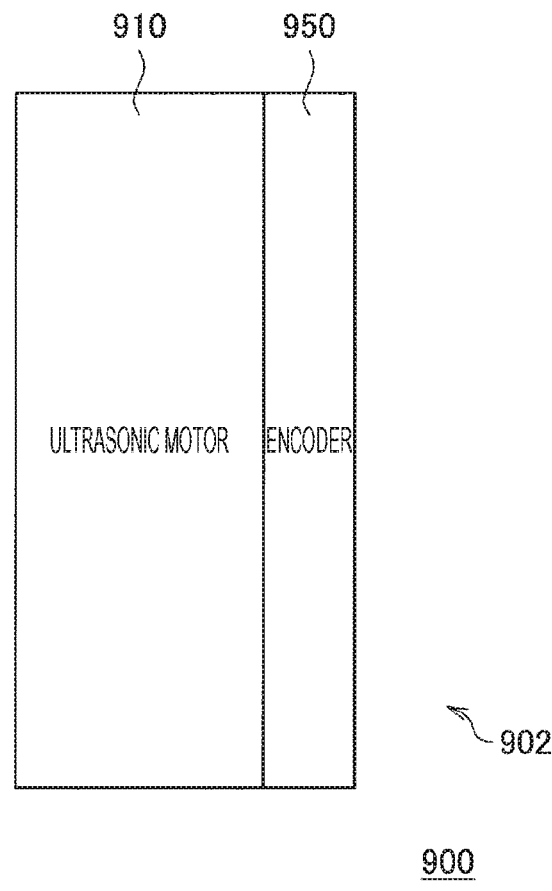
FIG. 10 is a diagram schematically illustrating a schematic configuration of the actuator including the ultrasonic motor according to the embodiment.

FIG. 10 is a diagram schematically illustrating a schematic configuration 902 of the actuator 900 including the ultrasonic motor 910. As illustrated in FIG. 10, the actuator 900 of the present embodiment includes the ultrasonic motor 910 and the encoder 950 as main configuration elements. In general, an ultrasonic motor has characteristics that an output by a single motor is large and the number of rotations is low, and is used for direct drive or at a low reduction rate. For this reason, as illustrated in FIGS. 9 and 10, in a case where the actuator 900 does not include a speed reducer having nonlinear torque transmission characteristics, even a small external torque can be easily estimated.

Figure 11:
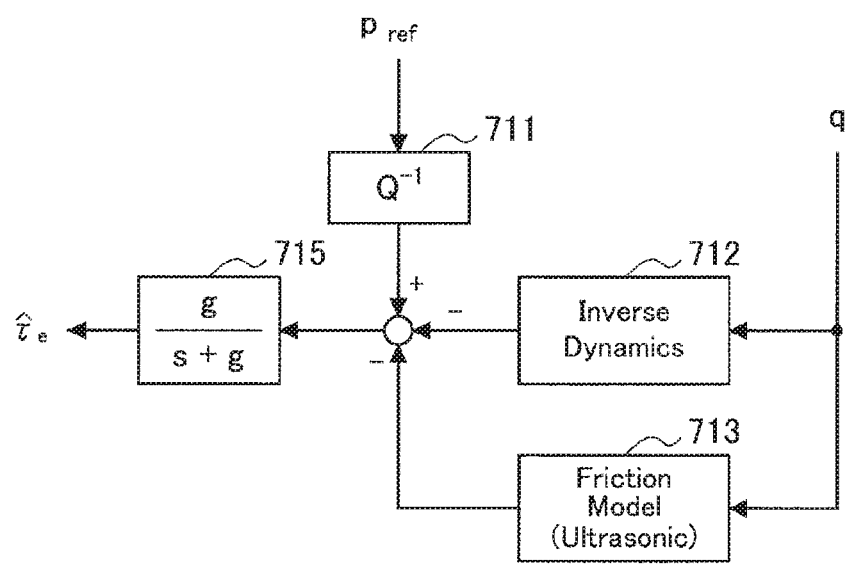
FIG. 11 is a diagram for describing external force estimation of a case where the actuator including the ultrasonic motor according to the embodiment is applied.

Furthermore, FIG. 11 is a diagram for describing external force estimation of the case where the actuator 900 including the ultrasonic motor 910 is applied. FIG. 11 schematically illustrates a conceptual arithmetic unit that performs various arithmetic operations according to the ultrasonic motor 910 in blocks. Note that, in the following description, differences from the external force estimation regarding the electromagnetic motor 810 will be mainly described, and detailed description of common configurations and functions will be omitted.

As described above, the block 711 is an arithmetic unit that calculates a torque value according to the type of the motor. In a traveling wave-type ultrasonic motor, control based on a phase difference is performed for two piezoelectric elements. More specifically, the frequency is fixed and the phase difference is controlled to be −90° to 90°. In the phase control regarding the ultrasonic motor, the phase becomes 0 when the motor torque is 0 but the stator 912 performs resonance vibration. Therefore, no rotational force is generated but the friction between the stator 912 and the rotor 914 becomes small. For this reason, the ultrasonic motor has a characteristic that the back drivability becomes smaller.

Therefore, in a case where the ultrasonic motor 910 is used for the drive of the joint units 421a to 421f, the block 711 calculates a phase difference command torque $\tau_{p\_ref}$ instead of the current command torque $\tau_{i\_ref}$ described with reference to FIG. 7.

Figure 12:
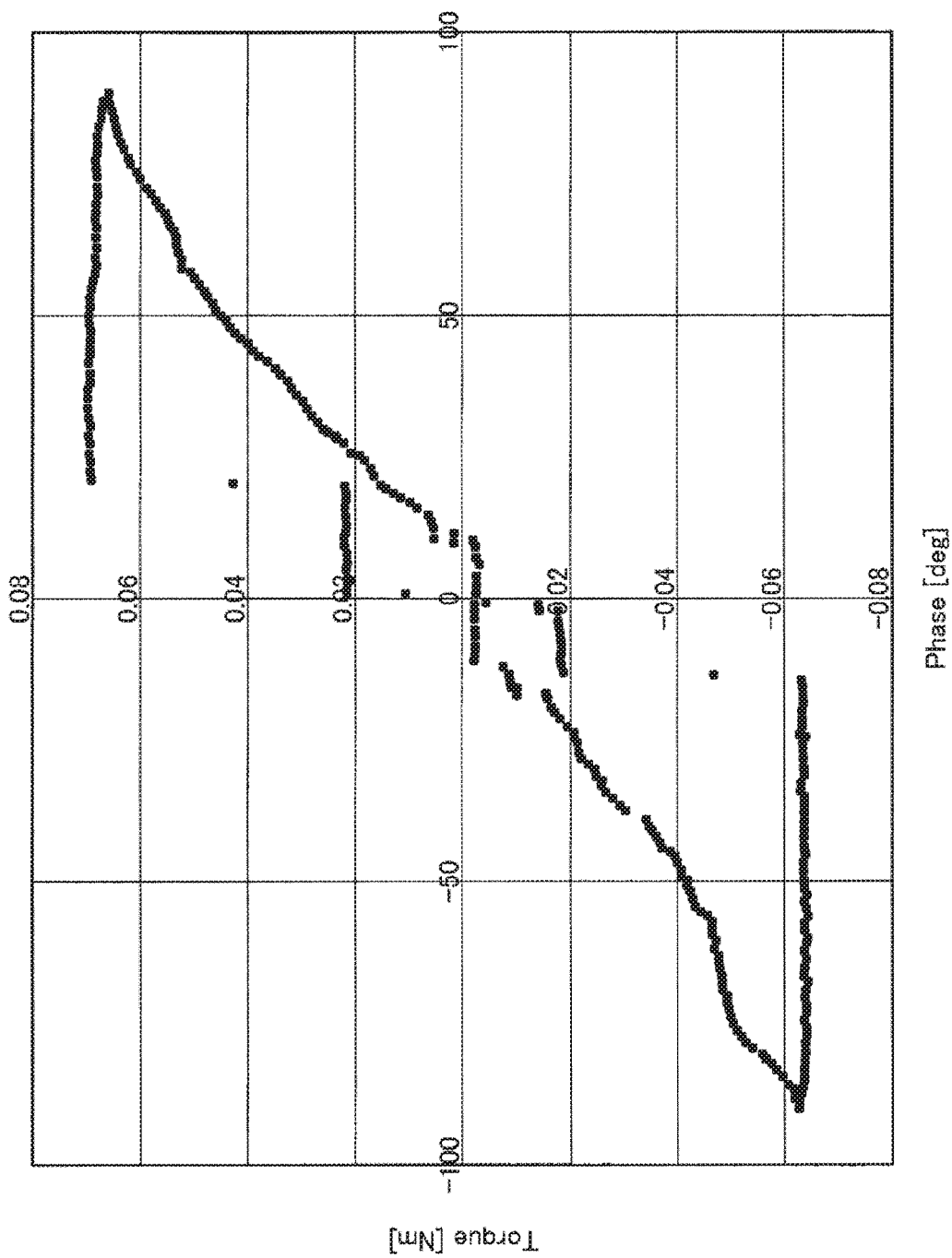
FIG. 12 is a graph illustrating a measurement result of an output torque of the ultrasonic motor according to a phase difference according to the embodiment.

FIG. 12 is a graph illustrating a measurement result of an output torque of the ultrasonic motor 910 according to the phase difference. As illustrated in FIG. 12, the output torque of the ultrasonic motor 910 is substantially linear with respect to the phase difference ($P_{ref}$). Therefore, the phase difference command torque $\tau_{p\_ref}$ can be modeled by the following mathematical expression (17).

[Math. 16]

$$\tau_{p\_ref} = K_p P_{ref} \quad (17)$$

Here, $K_p$ in mathematical expression (17) above represents a torque constant, and $P_{ref}$ represents the phase difference. In other words, in a case where the ultrasonic motor 910 is used for the drive of the joint units 421a to 421f, the block 711 can calculate the phase difference command torque $\tau_{p\_ref}$ by applying the above mathematical expression (17) to the input phase difference $P_{ref}$. Note that Q in FIG. 11 represents $Q=1/K_p$.

Furthermore, the control device 20 can calculate the motion estimation torque $\tau_{mt}$ on the basis of the characteristics of the ultrasonic motor 910 and estimate the final estimated external torque, similarly to the case of using the electromagnetic motor 810. According to the above function of the control device 20, when the ultrasonic motor 910 having a small influence of the back drivability, the estimated external torque can be estimated even in the case where the external torque is small, and initial light torque control can be realized without using a torque sensor. Furthermore, according to the control device 20, easier torque estimation can be realized without being affected by the nonlinear torque transmission characteristics regarding the speed reducer.

As described above, the control device 20 according to the present embodiment performs the arithmetic operation according to the type of the motor to enable the estimation of the external torque with high accuracy, and can realize the ideal joint control without using a torque sensor.

Note that, in the above description, the electromagnetic motor and the ultrasonic motor have been described as examples used for the drive of the joint units 421a to 421f. However, the type of the motor according to the present embodiment is not limited to the examples. The control device 20 according to the present embodiment can cope with various motors by performing arithmetic operations according to types as described above. As examples of the motor, an electrostatic force motor, a hydraulic motor, a pneumatic motor, and the like are assumed in addition to the above-described electromagnetic motor and ultrasonic motor.

Furthermore, the control device 20 according to the present embodiment is characterized in performing the arithmetic operation using the model identification result based on the measurement result, as described above. At this time, the control device 20 can improve the accuracy of the model by various methods.

For example, the control device 20 collects measurement values from a plurality of support arm devices 400 through a network, thereby efficiently accumulating data and performing highly accurate model identification.

Furthermore, the control device 20 may improve the accuracy of the model by machine learning, for example. At this time, the control device 20 may perform learning using the information such as angles, angular velocities, torque values, current values, and phase differences regarding the joint units 421a to 421f and sensor values collected by various sensors included in the support arm device 400. As the sensor value, for example, an acceleration sensor value or an external sensor value (three-dimensional measurement data, jig, or the like) is assumed.

Furthermore, the control device 20 can also perform learning using, for example, the external torque actually measured by the torque sensor as a teacher. The control device 20 can perform various types of learning using machine learning methods such as support vector machine (SVM), neural networks, regression models, or statistical methods.

The ideal joint control according to the present embodiment has been described in detail above. As described above, according to the control device 20 of the present embodiment, the torque control based on the estimated external force is realized and more various situations can be coped with.

More specifically, according to the control device 20 of the present embodiment, the cost for manufacturing and maintenance of the torque sensor can be reduced, and the total cost related to the introduction of the support arm device 400 can be reduced. Furthermore, according to the control device 20 of the present embodiment, the ideal joint control with high accuracy can be realized even in a case where arrangement of the torque sensor is difficult due to the environmental constraints and operation constraints.

Furthermore, according to the external force estimation by the control device 20 of the present embodiment, the arrangement of the torque sensor is not required. Therefore, an increase in cost for part replacement or the like, which may be caused due to malfunction or the like of the torque sensor, can be eliminated, and at the same time, the actuator and the support arm device 400 can be further downsized.

Note that the control device 20 according to the present embodiment may simultaneously control an actuator including a torque sensor and an actuator not including a torque sensor. For example, in the case of the support arm device 400 illustrated in FIG. 2, an actuator including a torque sensor is applied to the joint unit 421*f* or the like, close to the imaging unit 423, thereby realizing ideal joint control with higher reliability, and at the same time, an actuator not including a torque sensor is applied to the joint unit 421*a* close to the base unit 410, thereby reducing the total cost.

Furthermore, the control device 20 according to the present embodiment can simultaneously control the actuator 800 including the electromagnetic motor 810 and the actuator 900 including the ultrasonic motor 910. Thus, according to the technical idea of the present disclosure, appropriate actuators can be respectively adopted according to the environment and other requirements, and a more flexible device configuration and operation can be realized.

[2-4. Configuration of Support Arm System]

Next, a configuration of a support arm system according to the present embodiment in which the whole body coordination control and the ideal joint control described in [2-2. Generalized Inverse Dynamics] and [2-3. Ideal Joint Control] above are applied to the drive control of the support arm device will be described.

Figure 13:
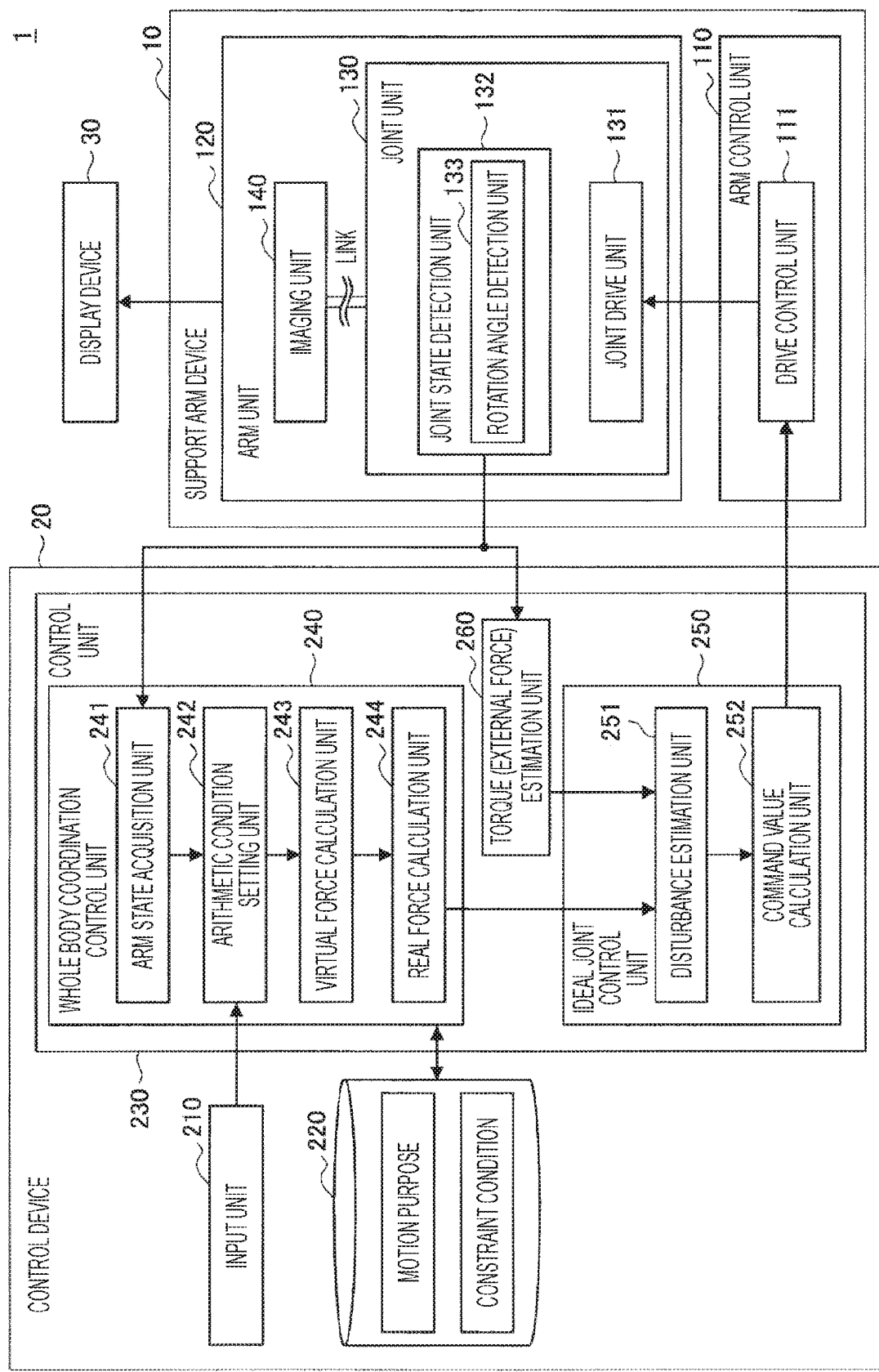
FIG. 13 is a functional block diagram illustrating a configuration example of a support arm system according to the embodiment.

A configuration example of a support arm system according to an embodiment of the present disclosure will be described with reference to FIG. 13. FIG. 13 is a functional block diagram illustrating a configuration example of a support arm system according to an embodiment of the present disclosure. Note that, in the support arm system illustrated in FIG. 13, a configuration related to drive control of an arm unit of a support arm device will be mainly illustrated.

Referring to FIG. 13, a support arm system 1 according to an embodiment of the present disclosure includes a support arm device 10, the control device 20, and a display device 30. In the present embodiment, the control device 20 performs various arithmetic operations in the whole body coordination control described in [2-2. Generalized Inverse Dynamics] and the ideal joint control described in [2-3. Ideal Joint Control] above, and controls drive of the arm unit of the support arm device 10 on the basis of arithmetic operation results. Furthermore, the arm unit of the support arm device 10 is provided with an imaging unit 140 described below, and an image captured by the imaging unit 140 is displayed on a display screen of the display device 30. Hereinafter, configurations of the support arm device 10, the control device 20, and the display device 30 will be described in detail.

The support arm device 10 includes the arm unit that is a multilink structure having a plurality of links connected by a joint unit including an actuator, and drives the arm unit within a movable range to control the position and posture of the distal end unit provided at the distal end of the arm unit. The support arm device 10 corresponds to the support arm device 400 illustrated in FIG. 2.

Referring to FIG. 13, the support arm device 10 includes an arm control unit 110 and an arm unit 120. Furthermore, the arm unit 120 includes a joint unit 130 and the imaging unit 140.

The arm control unit 110 integrally controls the support arm device 10 and controls drive of the arm unit 120. The arm control unit 110 corresponds to the control unit (not illustrated in FIG. 2) described with reference to FIG. 2. Specifically, the arm control unit 110 includes a drive control unit 111. Drive of the joint unit 130 is controlled by the control of the drive control unit 111, so that the drive of the arm unit 120 is controlled. More specifically, the drive control unit 111 controls a current amount to be supplied to a motor in an actuator of the joint unit 130 to control the number of rotations of the motor, thereby controlling a rotation angle and generated torque in the joint unit 130. However, as described above, the drive control of the arm unit 120 by the drive control unit 111 is performed on the basis of the arithmetic operation result in the control device 20. Therefore, the current amount to be supplied to the motor in the actuator of the joint unit 130, which is controlled by the drive control unit 111, is a current amount determined on the basis of the arithmetic operation result in the control device 20.

The arm unit 120 is a multilink structure including a plurality of joints and a plurality of links, and driving of the arm unit 120 is controlled by the control of the arm control unit 110. The arm unit 120 corresponds to the arm unit 420 illustrated in FIG. 2. The arm unit 120 includes the joint unit 130 and the imaging unit 140. Note that, since functions and configurations of the plurality of joint units included in the arm unit 120 are similar to one another, FIG. 13 illustrates a configuration of one joint unit 130 as a representative of the plurality of joint units.

The joint unit 130 rotatably connects the links with each other in the arm unit 120, and drives the arm unit 120 as rotational drive of the joint unit 130 is controlled by the control of the arm control unit 110. The joint unit 130 corresponds to the joint units 421*a* to 421*f* illustrated in FIG. 2. Furthermore, the joint unit 130 includes an actuator, and the configuration of the actuator is similar to the configuration illustrated in FIGS. 6, 10, and the like, for example.

The joint unit 130 includes a joint drive unit 131 and a joint state detection unit 132.

The joint drive unit 131 is a drive mechanism in the actuator of the joint unit 130, and the joint unit 130 is rotationally driven as the joint drive unit 131 is driven. The drive of the joint drive unit 131 is controlled by the drive control unit 111.

The joint state detection unit 132 detects a state of the joint unit 130. Here, the state of the joint unit 130 may mean a state of motion of the joint unit 130. For example, the state of the joint unit 130 includes information of the rotation angle, rotation angular speed, rotation angular acceleration, and the like of the joint unit 130. The joint state detection unit 132 transmits the detected state of the joint unit 130 to the control device 20.

The imaging unit 140 is an example of the distal end unit provided at the distal end of the arm unit 120, and acquires an image of a capture target. The imaging unit 140 corresponds to the imaging unit 423 illustrated in FIG. 2. Specifically, the imaging unit 140 is a camera or the like that can capture the capture target in the form of a moving image or a still image. More specifically, the imaging unit 140 includes a plurality of light receiving elements arrayed in a two dimensional manner, and can obtain an image signal indicating an image of the capture target by photoelectric conversion in the light receiving elements. The imaging unit 140 transmits the acquired image signal to the display device 30.

Note that, as in the case of the support arm device 400 illustrated in FIG. 2, the imaging unit 423 is provided at the distal end of the arm unit 420, the imaging unit 140 is actually provided at the distal end of the arm unit 120 in the support arm device 10. FIG. 13 illustrates a state in which the imaging unit 140 is provided at a distal end of a final link via the plurality of joint units 130 and the plurality of links by schematically illustrating a link between the joint unit 130 and the imaging unit 140.

Note that, in the present embodiment, various medical instruments can be connected to the distal end of the arm unit 120 as the distal end unit. Examples of the medical instruments include various treatment instruments such as a scalpel and forceps, and various units used in treatment, such as a unit of various detection devices such as probes of an ultrasonic examination device. Furthermore, in the present embodiment, the imaging unit 140 illustrated in FIG. 13 or a unit having an imaging function such as an endoscope or a microscope may also be included in the medical instruments. Thus, the support arm device 10 according to the present embodiment can be said to be a medical support arm device provided with medical instruments. Similarly, the support arm system 1 according to the present embodiment can be said to be a medical support arm control system. Note that the support arm device 10 illustrated in FIG. 13 can also be said to be a VM support arm device provided with a unit having an imaging function as the distal end unit. Furthermore, a stereo camera having two imaging units (camera units) may be provided at the distal end of the arm unit 120, and may capture an imaging target to be displayed as a 3D image.

The function and configuration of the support arm device 10 have been described above. Next, a function and a configuration of the control device 20 will be described. Referring to FIG. 13, the control device 20 includes an input unit 210, a storage unit 220, and a control unit 230.

The control unit 230 integrally controls the control device 20 and performs various operations for controlling the drive of the arm unit 120 in the support arm device 10. Specifically, to control the drive of the arm unit 120 of the support arm device 10, the control unit 230 performs various arithmetic operations in the whole body coordination control and the ideal joint control. Hereinafter, the function and configuration of the control unit 230 will be described in detail. The whole body coordination control and the ideal joint control have been already described in [2-2. Generalized Inverse Dynamics] and [2-3. Ideal Joint Control] above, and thus detailed description is omitted here.

The control unit 230 includes a whole body coordination control unit 240, an ideal joint control unit 250, and an external force estimation unit 260.

The whole body coordination control unit 240 performs various operations regarding the whole body coordination control using the generalized inverse dynamics. In the present embodiment, the whole body coordination control unit 240 acquires a state (arm state) of the arm unit 120 on the basis of the state of the joint unit 130 detected by the joint state detection unit 132. Furthermore, the whole body coordination control unit 240 calculates a control value for the whole body coordination control of the arm unit 120 in an operation space, using the generalized inverse dynamics, on the basis of the arm state, and a motion purpose and a constraint condition of the arm unit 120. Note that the operation space is a space for describing the relationship between the force acting on the arm unit 120 and the acceleration generated in the arm unit 120, for example.

The whole body coordination control unit 240 includes an arm state acquisition unit 241, an arithmetic condition setting unit 242, a virtual force calculation unit 243, and a real force calculation unit 244.

The arm state acquisition unit 241 acquires the state (arm state) of the arm unit 120 on the basis of the state of the joint unit 130 detected by the joint state detection unit 132. Here, the arm state may mean the state of motion of the arm unit 120. For example, the arm state includes information such as the position, speed, and acceleration of the arm unit 120. As described above, the joint state detection unit 132 acquires, as the state of the joint unit 130, the information of the rotation angle, rotation angular speed, rotation angular acceleration, and the like in each joint unit 130. Furthermore, although to be described below, the storage unit 220 stores various types of information to be processed by the control device 20. In the present embodiment, the storage unit 220 may store various types of information (arm information) regarding the arm unit 120, for example, the number of joint units 130 and links configuring the arm unit 120, connection states between the links and the joint units 130, and lengths of the links, and the like. The arm state acquisition unit 241 can acquire the arm information from the storage unit 220. Therefore, the arm state acquisition unit 241 can acquire, as the arm state, information such as the positions (coordinates) in the space of the plurality of joint units 130, the plurality of links, and the imaging unit 140 (in other words, the shape of the arm unit 120 and the position and posture of the imaging unit 140), and the forces acting on the joint units 130, the links, and the imaging unit 140, on the basis of the state and the arm information of the joint units 130. The arm state acquisition unit 241 transmits the acquired arm information to the arithmetic condition setting unit 242.

The arithmetic condition setting unit 242 sets arithmetic conditions in an operation regarding the whole body coordination control using the generalized inverse dynamics. Here, the arithmetic conditions may be a motion purpose and a constraint condition. The motion purpose may be various types of information regarding the motion of the arm unit 120. Specifically, the motion purpose may be target values of the position and posture (coordinates), speed, acceleration, force, and the like of the imaging unit 140, or target values of the positions and postures (coordinates), speeds, accelerations, forces, and the like of the plurality of joint units 130 and the plurality of links of the arm unit 120. Furthermore, the constraint condition may be various types of information that restricts (restrains) the motion of the arm unit 120. Specifically, the constraint condition may be coordinates of a region where each configuration component of the arm unit cannot move, an unmovable speed, a value of acceleration, a value of an ungenerable force, and the like. Furthermore, restriction ranges of various physical quantities under the constraint condition may be set according to inability to structurally realizing the arm unit 120 or may be appropriately set by the user. Furthermore, the arithmetic condition setting unit 242 includes a physical model for the structure of the arm unit 120 (in which, for example, the number and lengths of the links configuring the arm unit 120, the connection states of the links via the joint units 130, the movable ranges of the joint units 130, and the like are modeled), and may set a motion condition and the constraint condition by generating a control model in which the desired motion condition and constraint condition are reflected in the physical model.

In the present embodiment, appropriate setting of the motion purpose and the constraint condition enables the arm unit 120 to perform a desired motion. For example, not only the imaging unit 140 can be moved to a target position by setting a target value of the position of the imaging unit 140 as the motion purpose but also the arm unit 120 can be driven by providing a constraint of movement by the constraint condition, for example, to prevent the arm unit 120 from intruding into a predetermined region in the space.

A specific example of the motion purpose includes, for example, a pivot motion, which is a turning motion with an axis of a cone as a pivot axis, in which the imaging unit 140 moves in a conical surface setting an operation site as a vertex in a state where the capture direction of the imaging unit 140 is fixed to the operation site. Furthermore, in the pivot motion, the turning motion may be performed in a state where the distance between the imaging unit 140 and a point corresponding to the vertex of the cone is kept constant. By performing such a pivot motion, an observation site can be observed from an equal distance and at different angles, whereby the convenience of the user who performs surgery can be improved.

Furthermore, as another specific example, the motion purpose may be content to control the generated torque in each joint unit 130. Specifically, the motion purpose may be a power assist motion to control the state of the joint unit 130 to cancel the gravity acting on the arm unit 120, and further control the state of the joint unit 130 to support the movement of the arm unit 120 in a direction of a force provided from the outside. More specifically, in the power assist motion, the drive of each joint unit 130 is controlled to cause each joint unit 130 to generate a generated torque that cancels the external torque due to the gravity in each joint unit 130 of the arm unit 120, whereby the position and posture of the arm unit 120 are held in a predetermined state. In a case where an external torque is further added from the outside (for example, from the user) in the aforementioned state, the drive of each joint unit 130 is controlled to cause each joint unit 130 to generate a generated torque in the same direction as the added external torque. By performing such a power assist motion, the user can move the arm unit 120 with a smaller force in a case where the user manually moves the arm unit 120. Therefore, a feeling as if the user moved the arm unit 120 under weightlessness can be provided to the user. Furthermore, the above-described pivot motion and the power assist motion can be combined.

Here, in the present embodiment, the motion purpose may mean an action (motion) of the arm unit 120 realized by the whole body coordination control or may mean an instantaneous motion purpose in the action (in other words, a target value in the motion purpose). For example, in the above-described pivot motion, the imaging unit 140 performing the pivot motion itself is the motion purpose. In the act of performing the pivot motion, values of the position, speed, and the like of the imaging unit 140 in a conical surface in the pivot motion are set as the instantaneous motion purpose (the target values in the motion purpose). Furthermore, in the above-described power assist motion, for example, performing the power assist motion to support the movement of the arm unit 120 in the direction of the force applied from the outside itself is the motion purpose. In the act of performing the power assist motion, the value of the generated torque in the same direction as the external torque applied to each joint unit 130 is set as the instantaneous motion purpose (the target value in the motion purpose). The motion purpose in the present embodiment is a concept including both the instantaneous motion purpose (for example, the target values of the positions, speeds, forces, and the like of the configuration members of the arm unit 120 at a certain time) and the operations of the configuration members of the arm unit 120 realized over time as a result of the instantaneous motion purpose having been continuously achieved. The instantaneous motion purpose is set each time in each step in an arithmetic operation for the whole body coordination control in the whole body coordination control unit 240, and the arithmetic operation is repeatedly performed, so that the desired motion purpose is finally achieved.

Note that, in the present embodiment, the viscous drag coefficient in a rotational motion of each joint unit 130 may be appropriately set when the motion purpose is set. As described above, the joint unit 130 according to the present embodiment is configured to be able to appropriately adjust the viscous drag coefficient in the rotation motion of the actuator 430. Therefore, by setting the viscous drag coefficient in the rotational motion of each joint unit 130 when setting the motion purpose, an easily rotatable state or a less easily rotatable state can be realized for the force applied from the outside, for example. For example, in the above-descried power assist motion, when the viscous drag coefficient in the joint unit 130 is set to be small, a force required by the user to move the arm unit 120 can be made small, and a weightless feeling provided to the user can be promoted. As described above, the viscous drag coefficient in the rotational motion of each joint unit 130 may be appropriately set according to the content of the motion purpose.

Here, in the present embodiment, as will be described below, the storage unit 220 may store parameters regarding the operation conditions such as the motion purpose and the constraint condition used in the operation regarding the whole body coordination control. The arithmetic condition setting unit 242 can set the constraint condition stored in the storage unit 220 as the constraint condition used for the operation of the whole body coordination control.

Furthermore, in the present embodiment, the arithmetic condition setting unit 242 can set the motion purpose by a plurality of methods. For example, the arithmetic condition setting unit 242 may set the motion purpose on the basis of the arm state transmitted from the arm state acquisition unit 241. As described above, the arm state includes information of the position of the arm unit 120 and information of the force acting on the arm unit 120. Therefore, for example, in a case where the user is trying to manually move the arm unit 120, information regarding how the user is moving the arm unit 120 is also acquired by the arm state acquisition unit 241 as the arm state. Therefore, the arithmetic condition setting unit 242 can set the position, speed, force, and the like to/at/with which the user has moved the arm unit 120, as the instantaneous motion purpose, on the basis of the acquired arm state. By thus setting the motion purpose, the drive of the arm unit 120 is controlled to follow and support the movement of the arm unit 120 by the user.

Furthermore, for example, the arithmetic condition setting unit 242 may set the motion purpose on the basis of an instruction input from the input unit 210 by the user. Although to be described below, the input unit 210 is an input interface for the user to input information, commands, and the like regarding the drive control of the support arm device 10 to the control device 20. In the present embodiment, the motion purpose may be set on the basis of an operation input from the input unit 210 by the user. Specifically, the input unit 210 has, for example, operation unit operated by the user, such as a lever and a pedal. The positions, speeds, and the like of the configuration members of the arm unit 120 may be set as the instantaneous motion purpose by the arithmetic condition setting unit 242 in response to an operation of the lever, pedal, or the like.

Moreover, for example, the arithmetic condition setting unit 242 may set the motion purpose stored in the storage unit 220 as the motion purpose used for the operation of the whole body coordination control. For example, in the case of the motion purpose that the imaging unit 140 stands still at a predetermined point in the space, coordinates of the predetermined point can be set in advance as the motion purpose. Furthermore, for example, in the case of the motion purpose that the imaging unit 140 moves on a predetermined trajectory in the space, coordinates of each point representing the predetermined trajectory can be set in advance as the motion purpose. As described above, in a case where the motion purpose can be set in advance, the motion purpose may be stored in the storage unit 220 in advance. Furthermore, in the case of the above-described pivot motion, for example, the motion purpose is limited to a motion purpose setting the position, speed, and the like in the conical surface as the target values. In the case of the power assist motion, the motion purpose is limited to a motion purpose setting the force as the target value. In the case where the motion purpose such as the pivot motion or the power assist motion is set in advance in this way, information regarding ranges, types and the like of the target values settable as the instantaneous motion purpose in such a motion purpose may be stored in the storage unit 220. The arithmetic condition setting unit 242 can also set the various types of information regarding such a motion purpose as the motion purpose.

Note that by which method the arithmetic condition setting unit 242 sets the motion purpose may be able to be appropriately set by the user according to the application of the support arm device 10 or the like. Furthermore, the arithmetic condition setting unit 242 may set the motion purpose and the constraint condition by appropriately combining the above-described methods. Note that a priority of the motion purpose may be set in the constraint condition stored in the storage unit 220, or in a case where there is a plurality of motion purposes different from one another, the arithmetic condition setting unit 242 may set the motion purpose according to the priority of the constraint condition. The arithmetic condition setting unit 242 transmits the arm state and the set motion purpose and constraint condition to the virtual force calculation unit 243.

The virtual force calculation unit 243 calculates a virtual force in the operation regarding the whole body coordination control using the generalized inverse dynamics. The processing of calculating the virtual force performed by the virtual force calculation unit 243 may be the series of processing described in, for example, (2-2-1. Virtual Force Calculation Processing) above. The virtual force calculation unit 243 transmits the calculated virtual force $f_v$ to the real force calculation unit 244.

The real force calculation unit 244 calculates a real force in the operation regarding the whole body coordination control using the generalized inverse dynamics. The processing of calculating the real force performed by the real force calculation unit 244 may be the series of processing described in, for example, (2-2-2. Real Force Calculation Processing) above. The real force calculation unit 244 transmits the calculated real force (generated torque) $\tau_a$ to the ideal joint control unit 250. Note that, as described above, in the present embodiment, the generated torque $\tau_a$ calculated by the real force calculation unit 244 is also referred to as a command torque or a control value in the sense of a command value to the joint unit 130 in the whole body coordination control.

The ideal joint control unit 250 performs various operations regarding the ideal joint control using the generalized inverse dynamics. In the present embodiment, the ideal joint control unit 250 corrects the influence of disturbance for the generated torque $\tau_a$ calculated by the real force calculation unit 244 to calculate the command torque $\tau_a$ realizing an ideal response of the arm unit 120. Note that the arithmetic processing performed by the ideal joint control unit 250 corresponds to the series of processing described in [2-3. Ideal Joint Control] above.

The ideal joint control unit 250 includes a disturbance estimation unit 251 and a command value calculation unit 252.

The disturbance estimation unit 251 calculates the disturbance estimation value $\tau_d$ on the basis of the command torque $\tau_a$, the estimated external torque $\hat{\tau}_e$ estimated by the external force estimation unit 260, and the rotation angular speed calculated from the rotation angle q detected by the rotation angle detection unit 133. Note that the command torque $\tau_a$ mentioned here is a command value that represents the generated torque in the arm unit 120 to be finally transmitted to the support arm device 10. Thus, the disturbance estimation unit 251 has a function corresponding to the disturbance observer 703 illustrated in FIG. 5.

The command value calculation unit 252 calculates the command torque $\tau_a$ that is a command value representing the torque to be generated in the arm unit 120 and finally transmitted to the support arm device 10, using the disturbance estimation value $\tau_d$ calculated by the disturbance estimation unit 251. Specifically, the command value calculation unit 252 adds the disturbance estimation value $\tau_d$ calculated by the disturbance estimation unit 251 to $\tau^{ref}$ calculated from the ideal model of the joint unit 130 described in the above mathematical expression (12) to calculate the command torque $\tau_a$. For example, in a case where the disturbance estimation value $\tau_d$ is not calculated, the command torque $\tau_a$ becomes the torque target value $\tau^{ref}$.

As described above, in the ideal joint control unit 250, the information is repeatedly exchanged between the disturbance estimation unit 251 and the command value calculation unit 252, so that the series of processing described with reference to FIG. 5 is performed. The ideal joint control unit 250 transmits the calculated command torque $\tau_a$ to the drive control unit 111 of the support arm device 10. The drive control unit 111 performs control to supply the current amount corresponding to the transmitted command torque $\tau_a$ to the motor in the actuator of the joint unit 130, thereby controlling the number of rotations of the motor and controlling the rotation angle and the generated torque in the joint unit 130.

The external force estimation unit 260 has a function to estimate the external force acting on the joint unit 130 on the basis of the drive characteristic of the actuator. At this time, the external force estimation unit 260 calculates the motion estimation torque related to the drive of the joint unit 130 and estimates the external torque on the basis of the motion estimation torque. Furthermore, as described above, in the case where the motor included in the actuator of the joint unit 130 is an electromagnetic motor, the external force estimation unit 260 may estimate the external torque on the basis of the current command torque related to the drive of the joint unit 130. Furthermore, in the case where the motor included in the actuator of the joint unit 130 is an ultrasonic motor, the external force estimation unit 260 may estimate the external torque on the basis of the phase difference command torque related to the drive of the joint unit 130.

Furthermore, the external force estimation unit 260 estimates the friction torque and the internal consumption torque related to the drive of the joint unit 130, and can calculate the motion estimation torque on the basis of the friction torque, the internal consumption torque, and the like. For example, in the case where the motor included in the actuator of the joint unit 130 is an electromagnetic motor, the external force estimation unit 260 may estimate the friction torque using the model identification result based on the static friction and dynamic friction of the speed reducer. Thus, the external force estimation unit 260 has a function corresponding to the block 707 illustrated in FIG. 5.

In the support arm system 1 according to the present embodiment, the drive control of the arm unit 120 in the support arm device 10 is continuously performed during work using the arm unit 120, so the above-described processing in the support arm device 10 and the control device 20 is repeatedly performed. In other words, the state of the joint unit 130 is detected by the joint state detection unit 132 of the support arm device 10 and transmitted to the control device 20. The control device 20 performs various operations regarding the whole body coordination control and the ideal joint control for controlling the drive of the arm unit 120 on the basis of the state of the joint unit 130, and the motion purpose and the constraint condition, and transmits the command torque $\tau_a$ as the arithmetic operation result to the support arm device 10. As described above, the above arithmetic operation includes an external torque estimation operation by the external force estimation unit 260. The support arm device 10 controls the drive of the arm unit 120 on the basis of the command torque $\tau_a$, and the joint state detection unit 132 detects again the state of the joint unit 130 during or after the drive.

Description about other configurations included in the control device 20 will be continued.

The input unit 210 is an input interface for the user to input information, commands, and the like regarding the drive control of the support arm device 10 to the control device 20. In the present embodiment, the drive of the arm unit 120 of the support arm device 10 may be controlled on the basis of the operation input from the input unit 210 by the user, and the position and posture of the imaging unit 140 may be controlled. Specifically, as described above, instruction information regarding the instruction of the drive of the arm input from the input unit 210 by the user is input to the arithmetic condition setting unit 242, so that the arithmetic condition setting unit 242 may set the motion purpose in the whole body coordination control on the basis of the instruction information. The whole body coordination control is performed using the motion purpose based on the instruction information input by the user as described above, so that the drive of the arm unit 120 according to the operation input of the user is realized.

Specifically, the input unit 210 includes operation unit operated by the user, such as a mouse, a keyboard, a touch panel, a button, a switch, a lever, and a pedal, for example. For example, in a case where the input unit 210 has a pedal, the user can control the drive of the arm unit 120 by operating the pedal with the foot. Therefore, even in a case where the user is performing treatment using both hands on the operation site of the patient, the user can adjust the position and posture of the imaging unit 140, in other words, the user can adjust a capture position and a capture angle of the operation site, by the operation of the pedal with the foot.

The storage unit 220 stores various types of information processed by the control device 20. In the present embodiment, the storage unit 220 can store various parameters used in the operation regarding the whole body coordination control and the ideal joint control performed by the control unit 230. For example, the storage unit 220 may store the motion purpose and the constraint condition used in the operation regarding the whole body coordination control by the whole body coordination control unit 240. The motion purpose stored in the storage unit 220 may be, as described above, a motion purpose that can be set in advance, such as, for example, the imaging unit 140 standing still at a predetermined point in the space. Furthermore, the constraint conditions may be set in advance by the user and stored in the storage unit 220 according to a geometric configuration of the arm unit 120, the application of the support arm device 10, and the like. Furthermore, the storage unit 220 may also store various types of information regarding the arm unit 120 used when the arm state acquisition unit 241 acquires the arm state. Moreover, the storage unit 220 may store the arithmetic operation result in the arithmetic operation regarding the whole body coordination control and the ideal joint control by the control unit 230, various numerical values calculated in the arithmetic operation process, and the like. As described above, the storage unit 220 may store any parameters regarding the various types of processing performed by the control unit 230, and the control unit 230 can perform various types of processing while mutually exchanging information with the storage unit 220.

The function and configuration of the control device 20 have been described above. Note that the control device 20 according to the present embodiment can be configured by, for example, various information processing devices (arithmetic processing devices) such as a personal computer (PC) and a server. Next, a function and a configuration of the display device 30 will be described.

The display device 30 displays the information on the display screen in various formats such as texts and images to visually notify the user of various types of information. In the present embodiment, the display device 30 displays the image captured by the imaging unit 140 of the support arm device 10 on the display screen. Specifically, the display device 30 has functions and configurations of an image signal processing unit (not illustrated) that applies various types of image processing to an image signal acquired by the imaging unit 140, a display control unit (not illustrated) that performs control to display an image based on the processed image signal on the display screen, and the like. Note that the display device 30 may have various functions and configurations that a display device generally has, in addition to the above-described functions and configurations. The display device 30 corresponds to the display device 550 illustrated in FIG. 1.

The functions and configurations of the support arm device 10, the control device 20, and the display device 30 according to the present embodiment have been described above with reference to FIG. 13. Each of the above-described configuration elements may be configured using general-purpose members or circuit, or may be configured by hardware specialized for the function of each constituent element. Furthermore, all the functions of the configuration elements may be performed by a CPU or the like. Therefore, the configuration to be used can be changed as appropriate according to the technical level of the time of carrying out the present embodiment.

As described above, according to the present embodiment, the arm unit 120 that is the multilink structure in the support arm device 10 has at least six degrees or more of freedom, and the drive of each of the plurality of joint units 130 configuring the arm unit 120 is controlled by the drive control unit 111. Then, a medical instrument is provided at the distal end of the arm unit 120. The drive of each of the joint units 130 is controlled as described above, so that the drive control of the arm unit 120 with a higher degree of freedom is realized, and the support arm device 10 with higher operability for the user is realized.

3. Hardware Configuration

Next, a hardware configuration of the support arm device 10 and the control device 20 according to the present embodiment illustrated in FIG. 13 will be described in detail with reference to FIG. 14. FIG. 14 is a functional block diagram illustrating a configuration example of a hardware configuration of the support arm device 10 and the control device 20 according to an embodiment of the present disclosure.

The support arm device 10 and the control device 20 mainly include a CPU 901, a ROM 903, and a RAM 905. Furthermore, the support arm device 10 and the control device 20 further include a host bus 907, a bridge 909, an external bus 911, an interface 913, an input device 915, an output device 917, a storage device 919, a drive 921, a connection port 923, and a communication device 925.

The CPU 901 functions as an arithmetic processing unit and a control device, and controls the entire operation or a part of the operation of the support arm device 10 and the control device 20 according to various programs recorded in the ROM 903, the RAM 905, the storage device 919, or a removable recording medium 927. The ROM 903 stores programs, operation parameters, and the like used by the CPU 901. The RAM 905 primarily stores the programs used by the CPU 901, parameters that appropriately change in execution of the programs, and the like. The CPU 901, the ROM 903, and the RAM 905 are mutually connected by the host bus 907 configured by an internal bus such as a CPU bus. In the present embodiment, the CPU 901 corresponds to, for example, the arm control unit 110 and the control unit 230 illustrated in FIG. 13. Note that the operation parameters include, for example, various parameters related to arithmetic conditions such as the motion purpose, constraint conditions, and the like used in the arithmetic operations regarding the whole body coordination control, the above-described arm information, the model identification results used for estimation of the external torque, and the like.

The host bus 907 is connected to the external bus 911 such as a peripheral component interconnect/interface (PCI) bus via the bridge 909. Furthermore, the input device 915, the output device 917, the storage device 919, the drive 921, the connection port 923, and the communication device 925 are connected to the external bus 911 via the interface 913.

The input device 915 is an operation unit operated by the user, such as a mouse, a keyboard, a touch panel, a button, a switch, a lever, and a pedal, for example. Furthermore, the input device 915 may be, for example, a remote control unit (so-called remote controller) using infrared rays or other radio waves or may be an externally connected device 929 such as a mobile phone or a PDA corresponding to the operation of the support arm device 10 and the control device 20. Moreover, the input device 915 is configured by, for example, an input control circuit for generating an input signal on the basis of information input by the user using the above-described operation unit and outputting the input signal to the CPU 901, or the like. The user of the support arm device 10 and the control device 20 operates the input device 915 to input various data to and instruct a processing operation to the support arm device 10 and the control device 20. In the present embodiment, the input device 915 corresponds to, for example, the input unit 210 illustrated in FIG. 13. Furthermore, in the present embodiment, the motion purpose in the drive of the arm unit 120 may be set by an operation input by the user via the input device 915, and the whole body coordination control may be performed according to the motion purpose.

The output device 917 is configured by a device that can visually or audibly notify the user of acquired information. Such devices include display devices such as a CRT display device, a liquid crystal display device, a plasma display device, an EL display device, a lamp, and the like, sound output devices such as a speaker and a headphone, and a printer device. The output device 917 outputs result obtained by various types of processing performed by the support arm device 10 and the control device 20, for example. Specifically, the display device displays the results of the various types of processing performed by the support arm device 10 and the control device 20 as texts or images. Meanwhile, the sound output device converts an audio signal including reproduced sound data, voice data, or the like into an analog signal and outputs the analog signal. In the present embodiment, various types of information regarding the drive control of the arm unit 120 may be output from the output device 917 in any format. For example, a moving locus of each configuration member of the arm unit 120 in the drive control of the arm unit 120 may be displayed on the display screen of the output device 917 in the form of a graph. Note that, for example, the display device 30 illustrated in FIG. 13 may be a device including a function and a configuration as a display device of the output device 917 and a configuration of a control unit for controlling the drive of the display device, or the like.

The storage device 919 is a device for data storage configured as an example of a storage unit of the support arm device 10 and the control device 20. The storage device 919 is configured by a magnetic storage device such as a hard disk drive (HDD), a semiconductor storage device, an optical storage device, a magneto-optical storage device, or the like, for example. The storage device 919 stores programs executed by the CPU 901, various data, and the like. In the present embodiment, the storage device 919 corresponds to, for example, the storage unit 220 illustrated in FIG. 13. Furthermore, in the present embodiment, the storage device 919 can store arithmetic conditions (motion purpose and constraint conditions) in the arithmetic operations regarding the whole body coordination control using the generalized inverse dynamics, and the support arm device 10 and the control device 20 may perform arithmetic operations regarding the whole body coordination control using the arithmetic conditions stored in the storage device 919.

The drive 921 is a reader/writer for recording media, and is built in or is externally attached to the support arm device 10 and the control device 20. The drive 921 reads out information recorded on the removable recording medium 927 such as a mounted magnetic disk, optical disk, magneto-optical disk, or semiconductor memory, and outputs the information to the RAM 905. Furthermore, the drive 921 can also write a record on the removable recording medium 927 such as the mounted magnetic disk, optical disk, magneto-optical disk, or semiconductor memory. The removable recording medium 927 is, for example, a DVD medium, an HD-DVD medium, a Blu-ray (registered trademark) medium, or the like. Furthermore, the removable recording medium 927 may be a compact flash (CF (registered trademark)), a flash memory, a secure digital (SD) memory card, or the like. Furthermore, the removable recording medium 927 may be, for example, an integrated circuit (IC) card on which a non-contact IC chip is mounted, an electronic device, or the like. In the present embodiment, various types of information regarding the drive control of the arm unit 120 may be read from the various removable recording media 927 or written to the various removable recording media 927 by the drive 921.

The connection port 923 is a port for directly connecting a device to the support arm device 10 and the control device 20. Examples of the connection port 923 include a universal serial bus (USB) port, an IEEE 1394 port, a small computer system interface (SCSI) port, and the like. Other examples of the connection port 923 include an RS-232C port, an optical audio terminal, a high-definition multimedia interface (HDMI) (registered trademark) port, and the like. By connecting the externally connected device 929 to the connection port 923, the support arm device 10 and the control device 20 directly acquires various data from the externally connected device 929 and provides various data to the externally connected device 929. In the present embodiment, various types of information regarding the drive control of the arm unit 120 may be read from the various externally connected devices 929 or written to the various externally connected devices 929 via the connection port 923.

The communication device 925 is, for example, a communication interface configured by a communication device for being connected to a communication network (network) 931, and the like The communication device 925 is, for example, a communication card for a wired or wireless local area network (LAN), Bluetooth (registered trademark), a wireless USB (WUSB), or the like. Furthermore, the communication device 925 may be a router for optical communication, a router for an asymmetric digital subscriber line (ADSL), a modem for various communications, or the like. The communication device 925 can transmit and receive signals and the like, for example, to and from the Internet and other communication devices in accordance with a predetermined protocol such as TCP/IP, for example. Furthermore, the communication network 931 connected to the communication device 925 is configured by a network or the like connected by wire or wirelessly, and may be, for example, the Internet, home LAN, infrared communication, radio wave communication, satellite communication, or the like. In the present embodiment, various types of information regarding the drive control of the arm unit 120 may be transmitted/received to/from other external devices via the communication network 931 by the communication device 925.

In the above, an example of the hardware configuration that can realize the functions of the support arm device 10 and the control device 20 according to the present embodiment of the present disclosure has been described. Each of the above-described configuration elements may be configured using general-purpose members or may be configured by hardware specialized for the function of each configuration element. Therefore, the hardware configuration to be used can be changed as appropriate according to the technical level of the time of carrying out the present embodiment. Note that, although not illustrated in FIG. 14, the support arm device 10 naturally includes various configurations corresponding to the arm unit 120 illustrated in FIG. 13.

Note that a computer program for realizing the functions of the support arm device 10, the control device 20, and the display device 30 according to the above-described present embodiment can be prepared and implemented in a personal computer or the like. Furthermore, a computer-readable recording medium in which such a computer program is stored can be provided. The recording medium is, for example, a magnetic disk, an optical disk, a magneto-optical disk, a flash memory, or the like. Furthermore, the above computer program may be delivered via, for example, a network without using a recording medium.

4. Conclusion

As described above, the control device 20 according to an embodiment of the present disclosure can estimate the external torque regarding the joint unit 130 of the support arm device 10 and can realize the ideal joint control based on the estimated estimated external torque. According to the configuration, the torque control based on the estimated external force is realized and more various situations can be coped with.

Although the favorable embodiments of the present disclosure have been described in detail with reference to the accompanying drawings, the technical scope of the present disclosure is not limited to such examples. It is obvious that persons having ordinary knowledge in the technical field of the present disclosure can conceive various modifications or alterations within the scope of the technical idea described in the claims, and the modifications and alterations are naturally understood to belong to the technical scope of the present disclosure.

Furthermore, the effects described in the present specification are merely illustrative or exemplary and are not restrictive. That is, the technology according to the present disclosure can exhibit other effects obvious to those skilled in the art from the description of the present specification together with or in place of the above-described effects.

Note that following configurations also belong to the technical scope of the present disclosure.

(1)

A medical support arm system including:
  a support arm that is a multilink structure having a plurality of links connected by a joint unit including an actuator, and configured to support a medical unit; and
  a control device including an external force estimation unit configured to estimate an external force acting on the joint unit on the basis of a drive characteristic of the actuator, and a joint control unit configured to control drive of the joint unit on the basis of an external torque estimated by the external force estimation unit.

(2)

The medical support arm system according to (1), in which
the external force estimation unit calculates a motion estimation torque related to the drive of the joint unit, and estimates the external torque on the basis of the motion estimation torque.

(3)

The medical support arm system according to (2), in which
the external force estimation unit estimates a friction torque related to the drive of the joint unit, and calculates the motion estimation torque on the basis of the friction torque.

(4)

The medical support arm system according to (3), in which
the external force estimation unit estimates the friction torque using a model identification result based on a static friction and a dynamic friction of a speed reducer.

(5)

The medical support arm system according to any one of (2) to (4), in which
the external force estimation unit estimates an internal consumption torque related to the drive of the joint unit, and calculates the motion estimation torque on the basis of the internal consumption torque.

(6)

The medical support arm system according to any one of (1) to (5), in which
the external force estimation unit estimates the external torque on the basis of a current command torque related to the drive of the joint unit.

(7)

The medical support arm system according to any one of (1) to (3), in which
the external force estimation unit estimates the external torque on the basis of a phase difference command torque related to the drive of the joint unit.

(8)

The medical support arm system according to any one of (1) to (6), in which
the joint control unit controls an electromagnetic motor that generates a drive force related to the drive of the joint unit.

(9)

The medical support arm system according to any one of (1) to 3 and 7, in which
the joint control unit controls an ultrasonic motor that generates a drive force related to the drive of the joint unit.

(10)

The medical support arm system according to any one of (1) to (9), in which
the support arm includes a first joint unit not including a torque sensor and a second joint unit including the torque sensor, and
the joint control unit performs drive control of the first joint unit based on the external torque estimated by the external force estimation unit and drive control of the second joint unit based on an external torque detected by the torque sensor.

(11)

The medical support arm system according to any one of (1) to (10), in which the actuator includes a first actuator including an electromagnetic motor that generates a drive force related to the drive of the joint unit, and a second actuator including an ultrasonic motor that generates a drive force related to the drive of the joint unit, and the joint control unit controls both the first actuator and the second actuator.

(12)

A medical support arm control method including:
by a processor, controlling drive of a joint unit including an actuator of a support arm that is a multilink structure having a plurality of links connected by the joint unit; and
estimating an external force acting on the joint unit on the basis of a drive characteristic of the actuator, in which
the controlling further includes controlling the drive of the joint unit on the basis of an estimated external torque.

(13)

A medical support arm control device including:
a joint control unit configured to control drive of a joint unit including an actuator of a support arm that is a multilink structure having a plurality of links connected by the joint unit; and
an external force estimation unit configured to estimate an external force acting on the joint unit on the basis of a drive characteristic of the actuator, in which
the joint control unit controls the drive of the joint unit on the basis of an external torque estimated by the external force estimation unit.

REFERENCE SIGNS LIST

1 Support arm system
10 Support arm device
20 Control device
30 Display device
110 Arm control unit
111 Drive control unit
120 Arm unit
130 Joint unit
131 Joint drive unit
132 Joint state detection unit
133 Rotation angle detection unit
140 Imaging unit
210 Input unit
220 Storage unit
230 Control unit
240 Whole body coordination control unit
241 Arm state acquisition unit
242 Arithmetic condition setting unit
243 Virtual force calculation unit
244 Real force calculation unit
250 Ideal joint control unit
251 Disturbance estimation unit
252 Command value calculation unit
260 External force estimation unit

The invention claimed is:
1. A medical support arm system, comprising:
a support arm configured to support a medical unit, wherein
the support arm is a multilink structure having a plurality of links,
the plurality of links is connected by a joint unit,
the joint unit includes an actuator, and
the actuator includes a motor and a speed reducer;
a control device that includes:
an external force estimation unit configured to:

estimate an external force on the joint unit based on a drive characteristic of the motor of the actuator, wherein the drive characteristic of the motor includes at least one of an inertia of the motor or a velocity of the motor;

estimate, using a model identification result, a friction torque associated with a drive of the joint unit based on a static friction and a dynamic friction of the speed reducer;

calculate a motion estimation torque associated with the drive of the joint unit based on the friction torque; and estimate an external torque on the joint unit based on the estimated external force, a current command torque associated with the drive of the joint unit, and the motion estimation torque; and a joint control unit configured to control the drive of the joint unit based on the estimated external torque.

2. The medical support arm system according to claim 1, wherein the external force estimation unit is further configured to:

estimate an internal consumption torque associated with the drive of the joint unit, and calculate the motion estimation torque based on the internal consumption torque.

3. The medical support arm system according to claim 1, wherein the current command torque is calculated based on an input current value and a torque constant.

4. A medical support arm control method, comprising:

in a medical support arm system that comprises a support arm, wherein the support arm includes a joint unit:

controlling, by a processor of the medical support arm system, a drive of the joint unit of the support arm, wherein the support arm has a plurality of links connected by the joint unit, the joint unit includes an actuator, and the actuator includes a motor, and a speed reducer;

estimating an external force on the joint unit based on a drive characteristic of the motor of the actuator, wherein the drive characteristic of the motor includes at least one of an inertia of the motor or a velocity of the motor;

estimating, using a model identification result, a friction torque associated with the drive of the joint unit based on a static friction and a dynamic friction of the speed reducer;

calculating a motion estimation torque associated with the drive of the joint unit based on the friction torque; and estimating an external torque on the joint unit based on the estimated external force, a current command torque associated with the drive of the joint unit, and the motion estimation torque; and controlling the drive of the joint unit based on the estimated external torque.

5. The medical support arm control method according to claim 4, further comprising:

estimating an internal consumption torque associated with the drive of the joint unit; and calculating the motion estimation torque based on the internal consumption torque.

6. The medical support arm control method according to claim 4, wherein the current command torque is calculated based on an input current value and a torque constant.

7. A medical support arm control device, comprising:

a joint control unit configured to control a drive of a joint unit of a support arm, wherein the support arm is a multilink structure having a plurality of links, the plurality of links is connected by the joint unit, the joint unit includes an actuator, and the actuator includes a motor, and a speed reducer; and an external force estimation unit configured to:

estimate an external force on the joint unit based on a drive characteristic of the motor of the actuator, wherein the drive characteristic of the motor includes at least one of an inertia of the motor or a velocity of the motor;

estimate, using a model identification result, a friction torque associated with the drive of the joint unit based on a static friction and a dynamic friction of the speed reducer;

calculate a motion estimation torque associated with the drive of the joint unit based on the friction torque; and estimate an external torque on the joint unit based on the estimated external force, a current command torque associated with the drive of the joint unit, and the motion estimation torque, wherein the joint control unit is further configured to control the drive of the joint unit based on the estimated external torque.

* * * * *